US006997913B2

(12) United States Patent
Wilkinson

(10) Patent No.: US 6,997,913 B2
(45) Date of Patent: Feb. 14, 2006

(54) NEEDLE SAFETY DEVICE

(75) Inventor: Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/740,978

(22) Filed: Dec. 19, 2003

(65) Prior Publication Data

US 2004/0133172 A1  Jul. 8, 2004

Related U.S. Application Data

(63) Continuation-in-part of application No. 10/165,407, filed on Jun. 7, 2002.

(51) Int. Cl.
*A61M 5/00* (2006.01)

(52) U.S. Cl. ...................... 604/263; 604/110
(58) Field of Classification Search ............... 604/110, 604/198, 263, 192, 187, 136
See application file for complete search history.

(56) References Cited

U.S. PATENT DOCUMENTS

| 3,463,152 A | 8/1969 | Sorenson |
| 3,572,334 A | 3/1971 | Petterson |
| 3,595,230 A | 7/1971 | Suyeoka et al. |
| 3,827,434 A | 8/1974 | Thompson et al. |
| 4,160,450 A | 7/1979 | Doherty |
| 4,170,993 A | 10/1979 | Alvarez |
| 4,354,491 A | 10/1982 | Marbry |
| 4,377,165 A | 3/1983 | Luther et al. |
| 4,664,654 A * | 5/1987 | Strauss .................. 604/198 |
| 4,676,783 A | 6/1987 | Jagger et al. |
| 4,681,567 A | 7/1987 | Masters et al. |
| 4,723,943 A | 2/1988 | Spencer |
| 4,747,831 A | 5/1988 | Kulli |
| 4,781,692 A | 11/1988 | Jagger et al. |
| 4,804,372 A | 2/1989 | Laico et al. |
| 4,813,426 A * | 3/1989 | Haber et al. ............... 600/576 |
| 4,826,490 A | 5/1989 | Byrne et al. |
| 4,867,746 A | 9/1989 | Dufresne |
| 4,884,560 A | 12/1989 | Kuracina |
| 4,887,998 A | 12/1989 | Martin et al. |
| 4,892,107 A * | 1/1990 | Haber .................. 600/576 |
| 4,917,669 A | 4/1990 | Bonaldo |
| 4,941,881 A | 7/1990 | Masters et al. |
| 4,946,446 A | 8/1990 | Vadher |
| 4,969,876 A | 11/1990 | Patterson |

(Continued)

FOREIGN PATENT DOCUMENTS

EP    0 268 445    5/1988

(Continued)

*Primary Examiner*—Sharon Kennedy
(74) *Attorney, Agent, or Firm*—Gerald Hespos, Esq.; Mark Lindsey

(57) ABSTRACT

A blood collection assembly includes a needle cannula with an intravenous end and a non-patient end. The cannula is mounted to a needle holder so that the non-patient end projects into the holder. A safety shield is telescoped over the needle cannula and is movable from a proximal position where the intravenous end of the cannula is exposed to a distal position where the intravenous end of the cannula is shielded. The safety shield is configured to be passively actuated and propelled into the distal position in response to insertion of a blood collection tube into the holder. However, a slide back actuator extends from the safety shield to permit the shield to be retracted into a proximal position during use and before the safety shield is locked in the distal position.

13 Claims, 24 Drawing Sheets

U.S. PATENT DOCUMENTS

| | | |
|---|---|---|
| 4,998,922 A | 3/1991 | Kuracina et al. |
| 5,037,402 A * | 8/1991 | Bartman .................. 604/198 |
| 5,084,030 A | 1/1992 | Byrne et al. |
| 5,088,986 A | 2/1992 | Nusbaum |
| 5,112,311 A | 5/1992 | Utterberg et al. |
| 5,120,320 A | 6/1992 | Fayngold |
| 5,185,006 A | 2/1993 | Williamitis et al. |
| 5,192,275 A | 3/1993 | Burns |
| 5,219,333 A | 6/1993 | Sagstetter et al. |
| 5,222,945 A | 6/1993 | Basnight |
| 5,246,428 A | 9/1993 | Falknor |
| 5,254,099 A | 10/1993 | Kuracina et al. |
| 5,261,880 A | 11/1993 | Streck et al. |
| 5,266,072 A | 11/1993 | Utterberg et al. |
| 5,269,765 A | 12/1993 | Kuracina |
| 5,295,975 A | 3/1994 | Lockwood, Jr. |
| 5,300,039 A | 4/1994 | Poulsen |
| 5,304,137 A | 4/1994 | Fluke |
| 5,318,547 A | 6/1994 | Altschuler .................. 604/198 |
| 5,389,085 A | 2/1995 | D'Alessio et al. |
| 5,411,487 A | 5/1995 | Castagna |
| 5,423,758 A * | 6/1995 | Shaw .................. 604/110 |
| 5,472,430 A | 12/1995 | Vaillancourt et al. |
| 5,484,421 A | 1/1996 | Smocer |
| 5,527,294 A | 6/1996 | Weatherford et al. |
| 5,536,257 A | 7/1996 | Byrne et al. |
| 5,549,558 A | 8/1996 | Martin |
| 5,549,572 A | 8/1996 | Byrne et al. |
| 5,562,624 A | 10/1996 | Righi et al. |
| 5,582,597 A | 12/1996 | Brimhall et al. |
| 5,601,535 A | 2/1997 | Byrne et al. |
| 5,616,135 A | 4/1997 | Thorne et al. |
| 5,718,239 A | 2/1998 | Newby et al. |
| 5,800,404 A | 9/1998 | Poulsen |
| 5,893,845 A | 4/1999 | Newby et al. |
| 6,013,059 A | 1/2000 | Jacobs .................. 604/198 |
| 6,261,265 B1 | 7/2001 | Mosseri |
| 6,409,706 B1 | 6/2002 | Loy .................. 604/198 |
| 6,805,689 B1 * | 10/2004 | Chen .................. 604/198 |
| 2003/0028149 A1 | 2/2003 | Sanpietro .................. 604/197 |

FOREIGN PATENT DOCUMENTS

| | | |
|---|---|---|
| EP | 0 286 992 | 10/1988 |
| EP | 0 299 287 | 1/1989 |
| EP | 0 680 767 | 11/1995 |
| EP | 1 316 325 A1 | 4/2003 |
| GB | 2 202 747 | 10/1988 |
| WO | WO 89/00865 | 2/1989 |

* cited by examiner

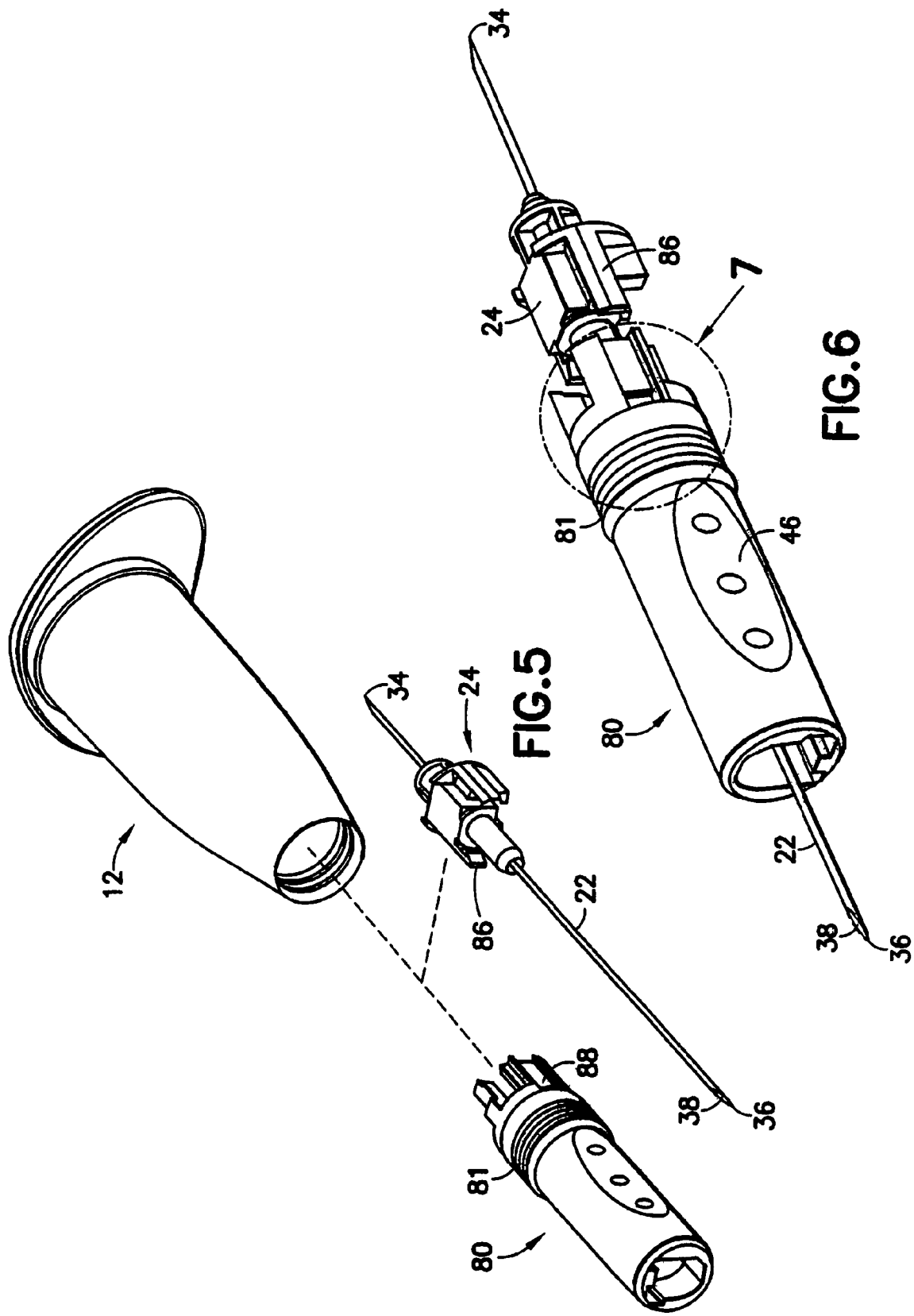

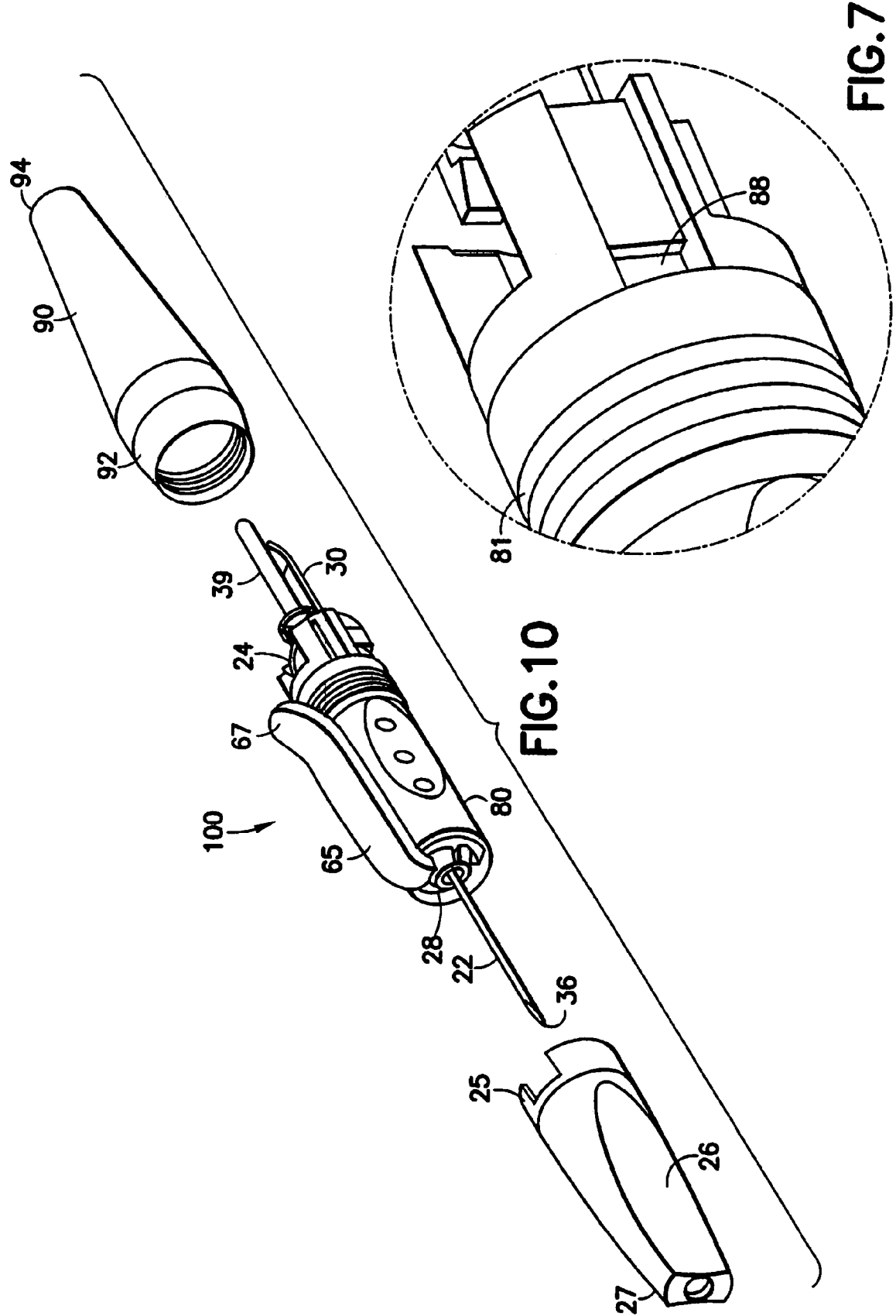

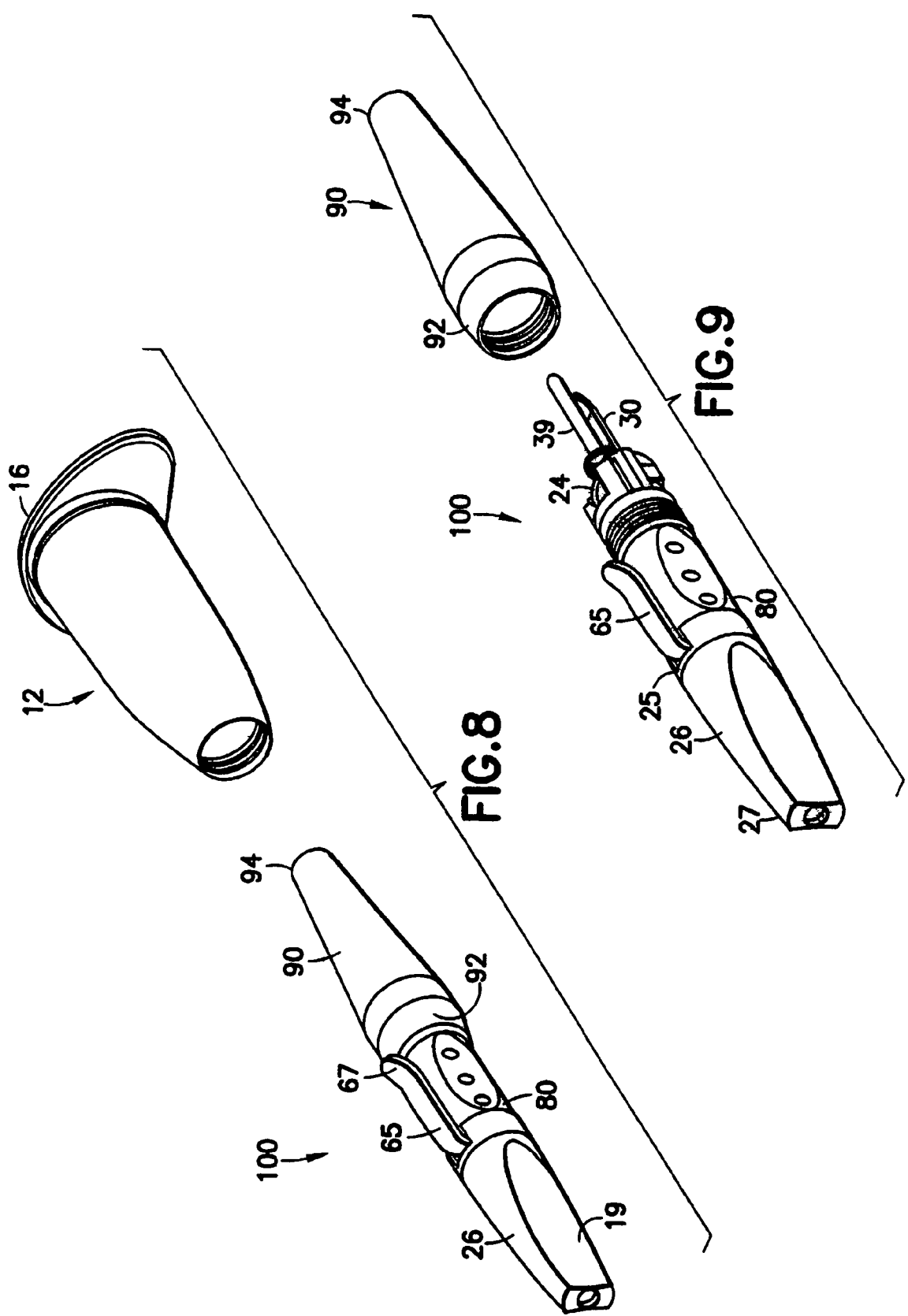

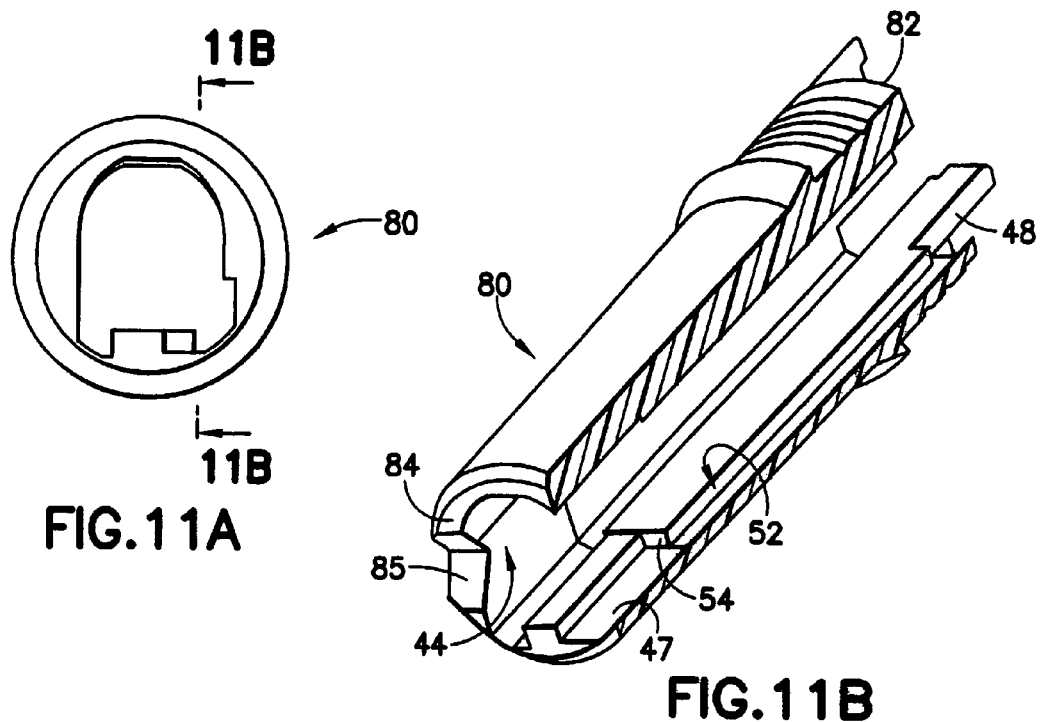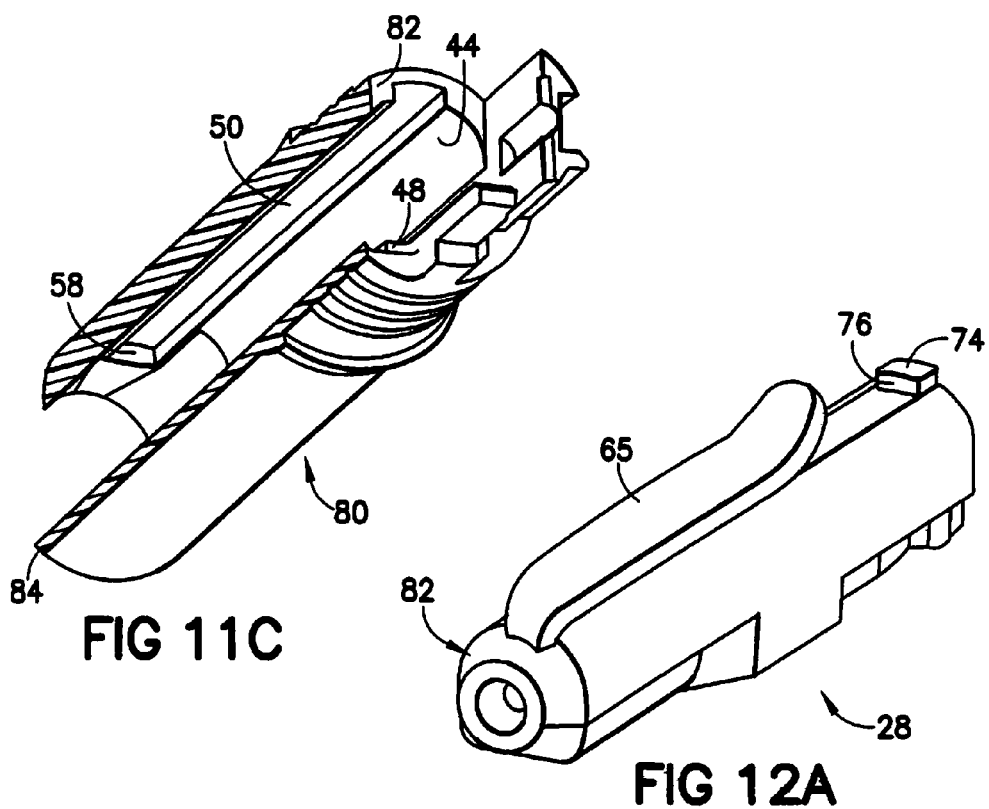

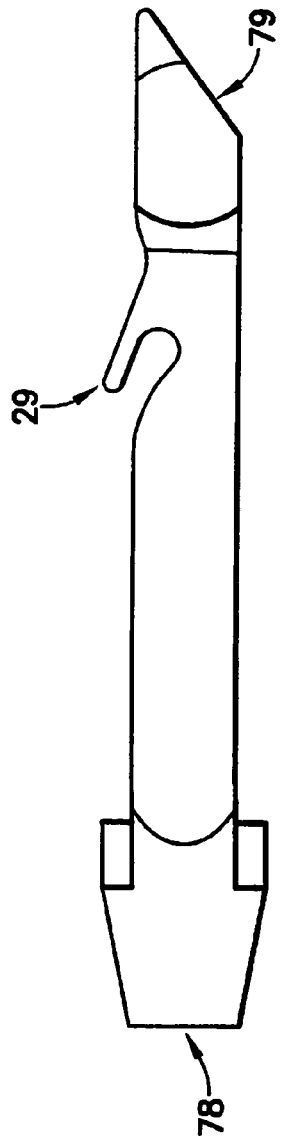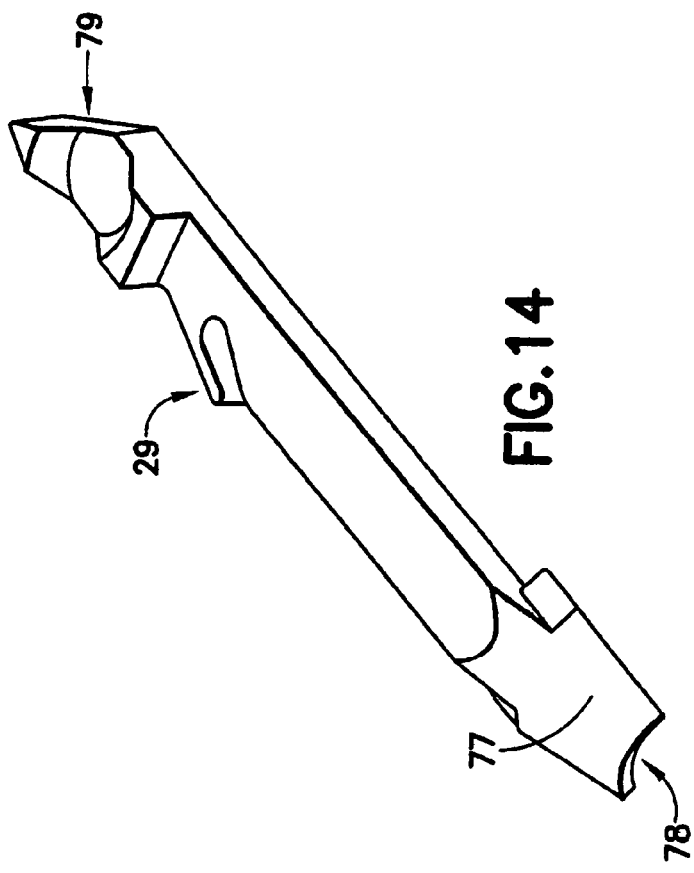

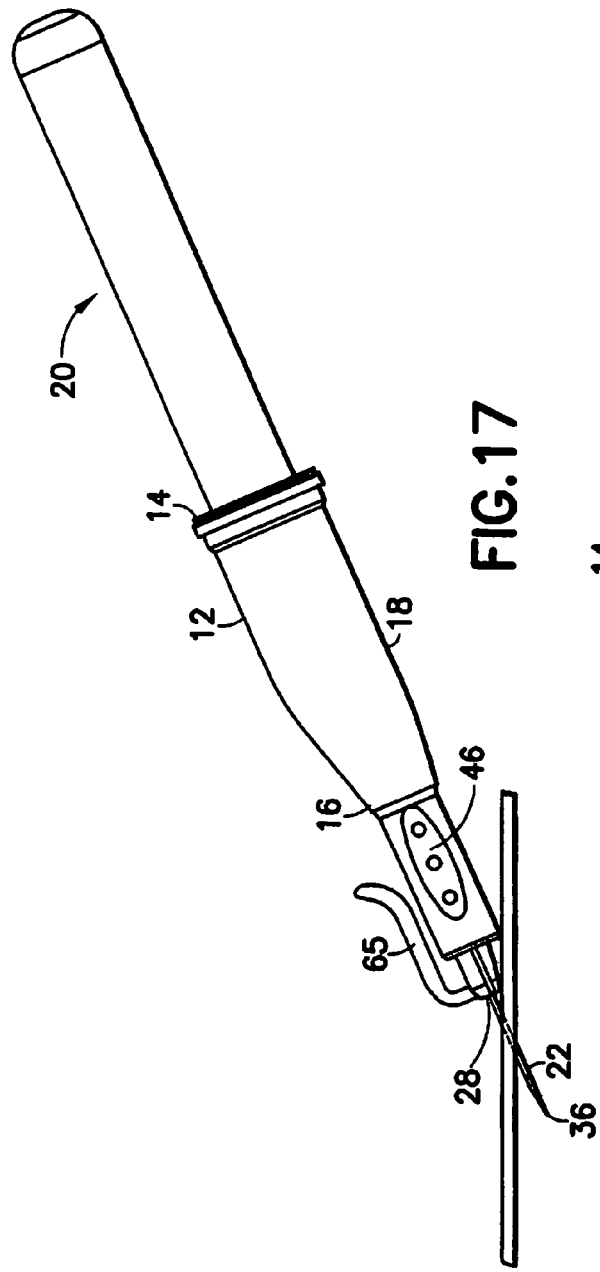
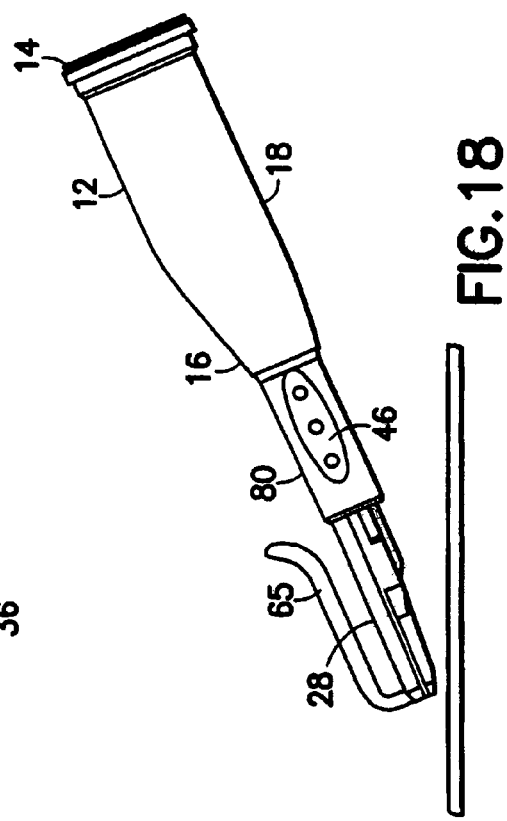

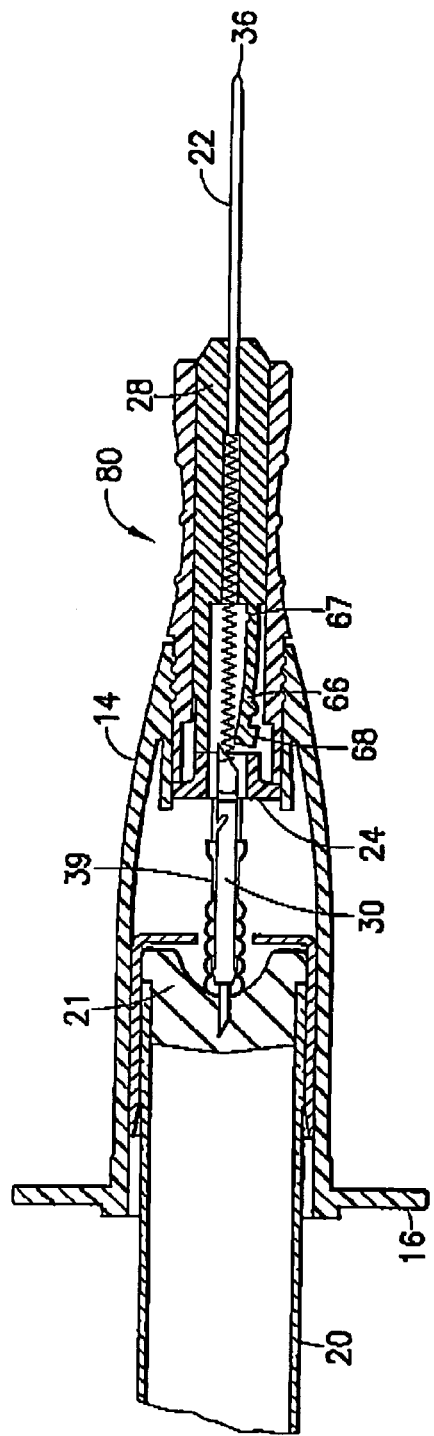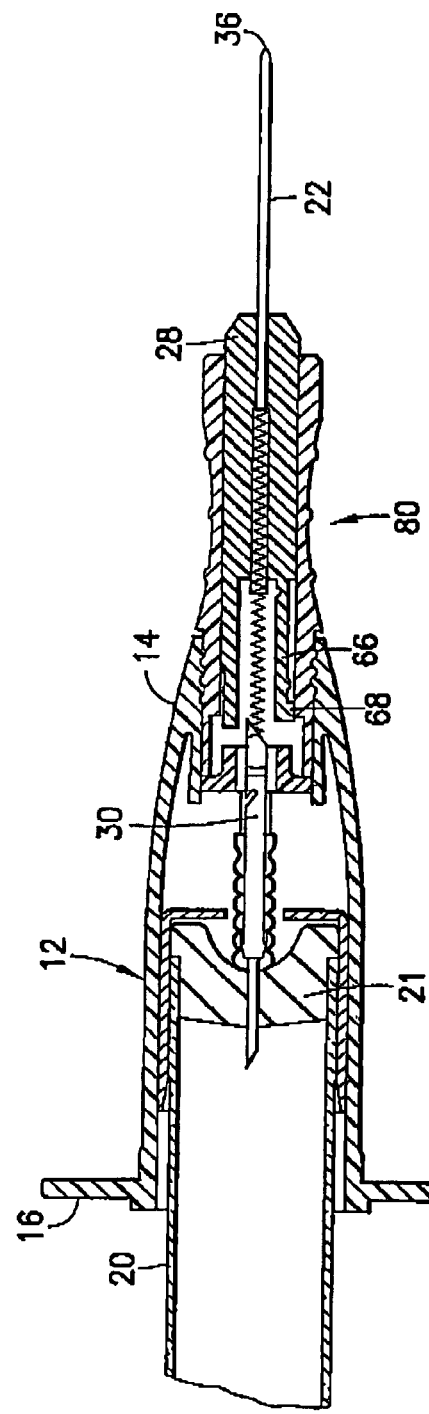

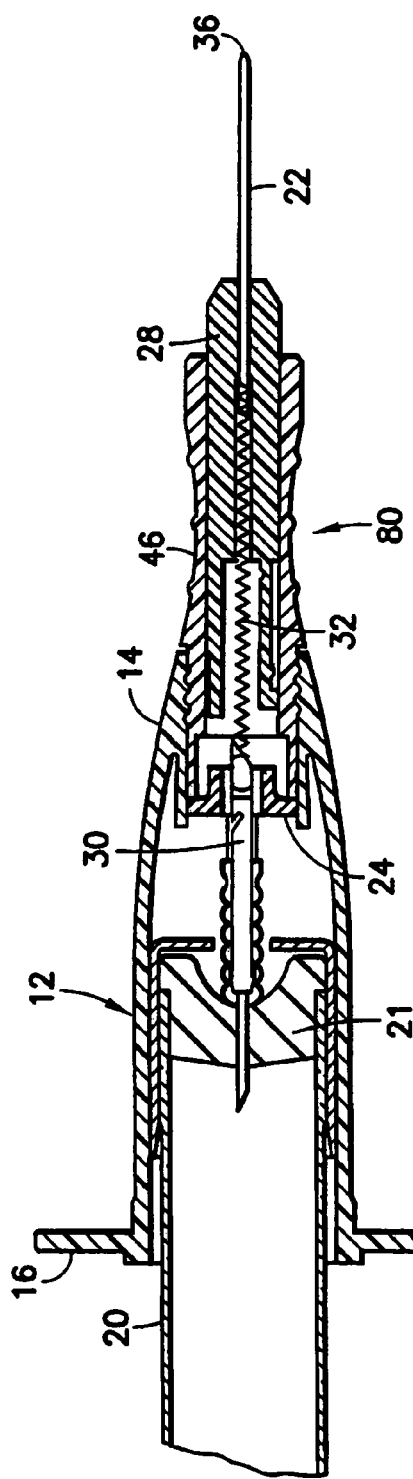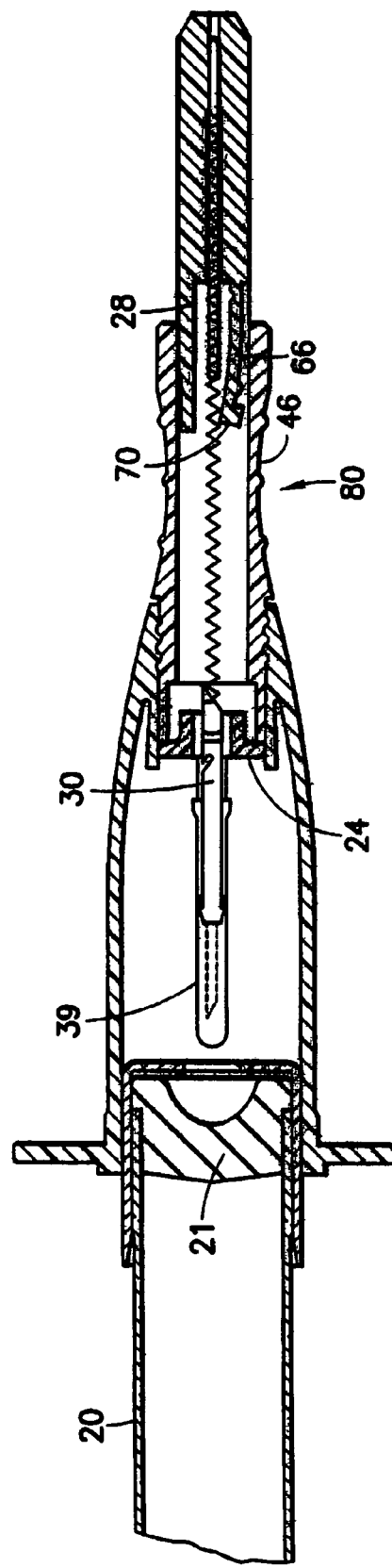

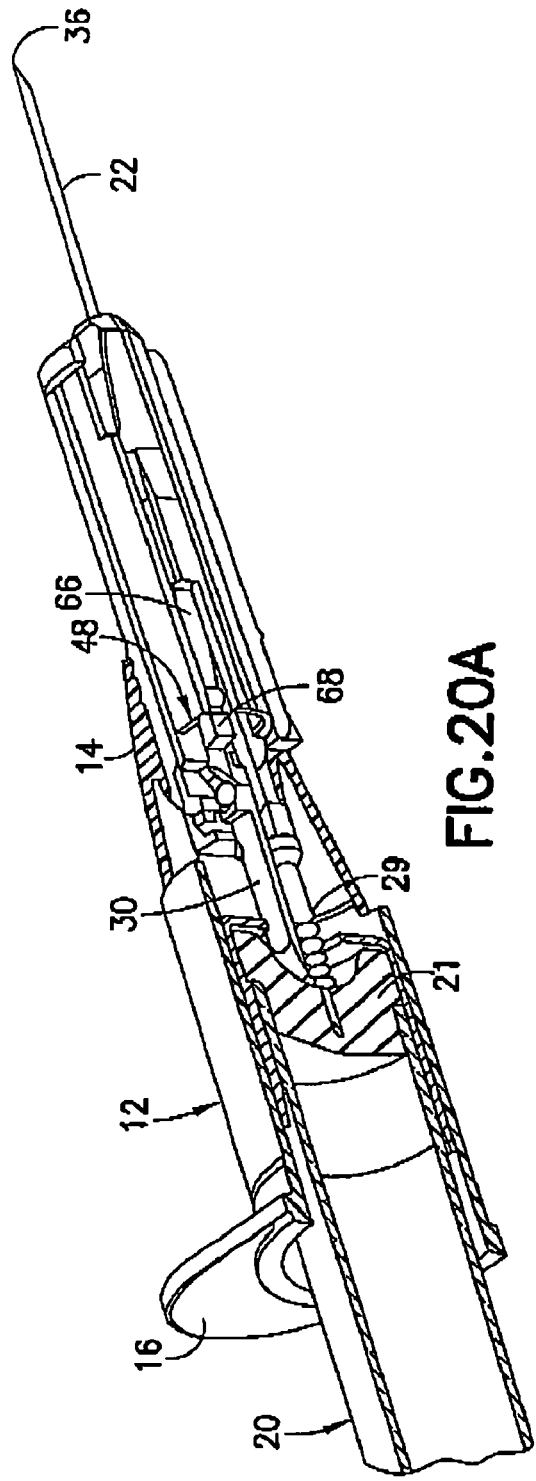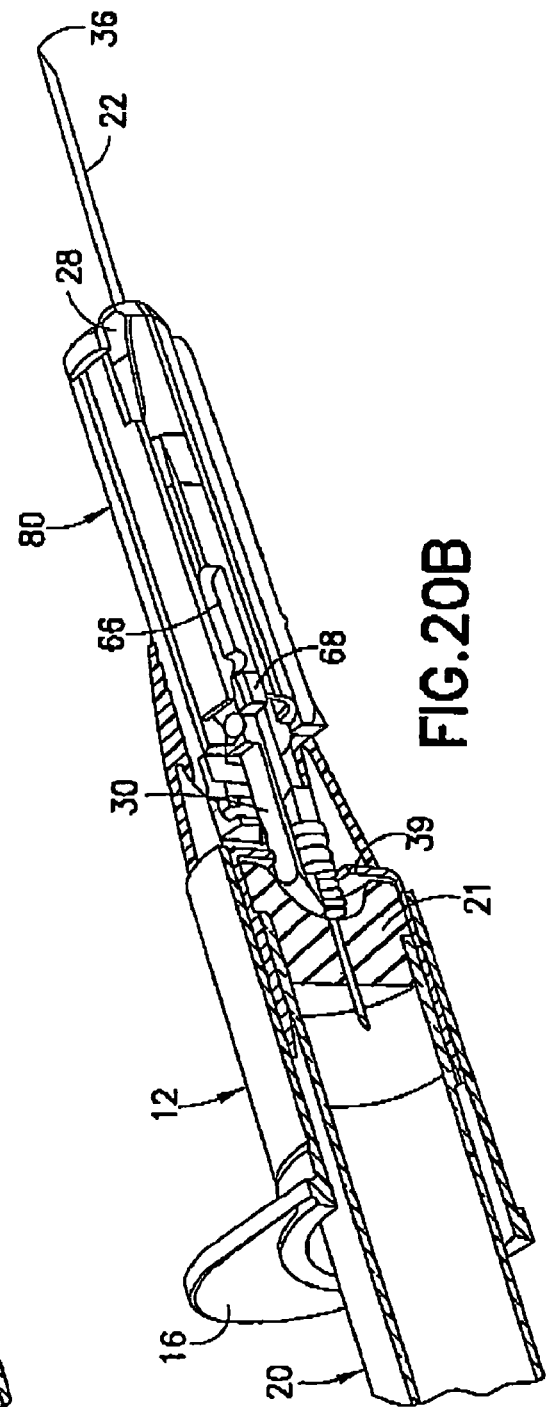

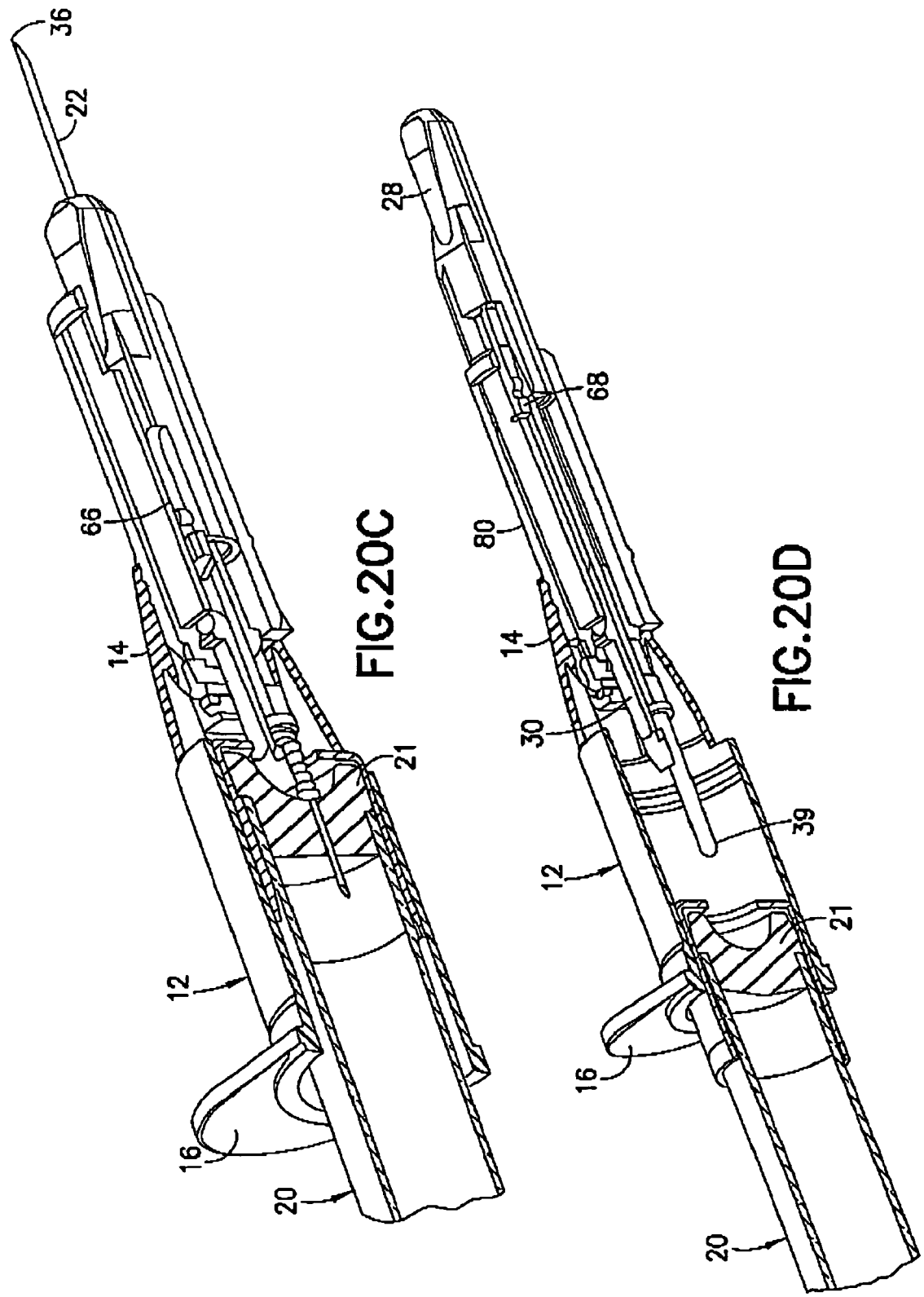

NEEDLE SAFETY DEVICE

RELATED APPLICATION

This application is a continuation-in-part of U.S. patent application Ser. No. 10/165,407, filed Jun. 7, 2002.

BACKGROUND OF THE INVENTION

1. Field of the Invention

The invention relates to a medical device with a needle cannula and a shield for passively shielding the needle cannula.

2. Description of the Related Art

A typical needle assembly includes a needle cannula having a proximal end, a pointed distal end and a lumen extending between the ends. A thermoplastic hub is mounted securely to the needle cannula at a location spaced from the distal end. The hub is provided with external threads or other surface configurations for removably mounting the prior art needle cannula on another structure. Some needle assemblies are used for drawing a sample of blood or other body fluid from a patient. The needle cannulas for these assemblies typically have pointed proximal and distal ends, and the needle hub is mounted to a location between the opposed ends of the needle cannula.

A needle assembly that is used to draw a sample of blood or other bodily fluid typically is used with a needle holder. The needle holder has a substantially tubular sidewall with a widely opened proximal end and a partly closed distal end. The hub of the prior art needle assembly can be engaged releasably with the partly closed distal end of the needle holder. Thus, the pointed proximal end of the needle cannula projects into the needle holder, while the pointed distal end of the needle cannula projects distally beyond the needle holder.

The combination of a needle assembly and a needle holder is used with an evacuated tube for drawing a sample of blood or other bodily fluid from a patient. The tube has a closed end, an open end, and a sidewall extending between the ends. The tube is evacuated, and the open end is sealed by a septum that retains the vacuum within the tube. The evacuated tube is dimensioned to be slid into the open proximal end of the needle holder. Sufficient sliding of the evacuated tube into the needle holder causes the proximal point of the needle cannula to pierce the septum of the evacuated tube. Thus, the needle cannula can be placed in communication with the interior of the evacuated tube.

The combination of a needle assembly, a needle holder and an evacuated tube is employed by initially urging the pointed distal end of the needle cannula into a blood vessel of a patient. Once the targeted blood vessel has been reached, the evacuated tube is urged into the needle holder so that the proximal point of the needle cannula pierces the septum on the tube. Low pressure conditions within the evacuated tube generate a flow of blood from the patient through the needle cannula and into the evacuated tube. The evacuated tube may be removed from the needle holder after a sufficient quantity of blood has been collected. One or more additional evacuated tubes may similarly be urged into the open end of the needle holder for drawing one or more additional samples of blood to be analyzed.

The needle cannula is withdrawn from the patient after a sufficient volume of blood has been collected for the required analytical procedures. The used needle cannula then must be shielded properly to avoid an accidental stick that could transmit a disease from the patient to the medical practitioner.

Many types of devices are available for shielding a used needle cannula. Some shields are hinged to the needle hub, and can be rotated from a first position, where the hinged shield is spaced from the needle cannula for use. After use, the hinged shield is rotated to a second position in shielding engagement around the needle cannula.

Other shields are telescoped over both the needle cannula and the needle hub. These shields initially are retained in a proximal position where the shield covers the hub but exposes the needle cannula for use. After use, the shield is telescoped distally to cover the needle cannula.

Most shielded needle assemblies are effective at performing their primary function of shielding a used needle cannula. However, many medical practitioners consider the available shieldable needle assemblies cumbersome. In particular, the shield that is telescoped over the needle hub typically will move relative to the needle cannula. Consequently, medical practitioners will grip the needle holder or other medical implement to which the shieldable needle assembly is mounted. However, a gripable region on the needle holder typically is relatively far from the distal end of the needle cannula and leads to at least a perception of poor control of the needle cannula. The perception of poor control increases as the length of the needle cannula is increased. As a result, needle assemblies with shields that telescope over the needle hub necessarily impose a limit on the length of the needle cannula that can be employed.

Additionally, in some cases, practitioners may be rushing and forget to operate the safety shield. Other situations arise where the patient moves suddenly or unexpectedly. Thus the needle cannula may inadvertently be pulled out of the vein and exposed with no time for the phlebotomist to initiate safety shielding. These weaknesses are not addressed adequately in prior art devices.

Successful venous entry depends partly upon the depth and angle of insertion of the needle cannula. A needle cannula that is inserted insufficiently may not reach a targeted blood vessel. Alternatively, a needle cannula can be inserted completely through a targeted blood vessel. Medical practitioners often judge the depth and angle of insertion of a needle cannula by monitoring the portions of the needle cannula that remain exposed between the skin of the patient and the hub of the needle assembly. The removal of a blood collection tube from a needle holder and the insertion of a new blood collection tube into the needle holder create forces along the axis of the needle cannula. These forces have the potential for varying the depth of insertion of the needle cannula. Accordingly, most medical practitioners monitor the section of the needle cannula that is exposed each time a blood collection tube is removed from the needle holder or inserted into the needle holder. Safety shields can impede the ability to visually monitor the depth of insertion of a needle cannula. Accordingly, an optimal safety shield will provide adequate safety against accidental sticks without obscuring the medical practitioner's view of the needle cannula between the skin of the patient and a reference point at or near the hub of the needle cannula.

SUMMARY OF THE INVENTION

The present invention is directed to a needle assembly with means for shielding the user or patient end of the needle cannula. The needle assembly includes a needle cannula having opposed proximal and distal ends and a lumen extending between the ends. At least the distal end of the needle cannula may be pointed.

The needle assembly further includes a hub surrounding portions of the needle cannula. The hub includes opposed proximal and distal ends that are disposed between the proximal and distal ends of the needle cannula. The hub may be mounted securely to the needle cannula. Additionally, the proximal end of the hub may be provided with external structure for releasable engagement with a needle holder or with some other medical implement.

The needle assembly further includes a housing that may be attached to the hub. The primary function of the housing is to provide guidance for a shield telescoped between the needle cannula and hub. The housing partially encloses the shield and constrains shield motion in a longitudinal direction, substantially co-axial with the needle cannula. Additionally, the housing further includes external surface configurations to assist the user in manipulating the device during venous punctures. The housing may have external structure for releasable engagement with a needle holder or with some other medical implement.

The above-referenced shield of the needle assembly surrounds the needle cannula and is telescoped into the housing. The shield initially is retained in a proximal position such that distal portions of the needle cannula are exposed for use. The shield can be moved from the proximal position to a distal position where the shield surrounds at least the pointed distal end of the needle cannula. The shield preferably is dimensioned to cover all of the needle cannula between the housing and the distal end of the needle cannula. Additionally, the shield preferably is constructed for locking engagement with the housing when the shield is in its distal position. Thus, the needle cannula cannot be re-exposed after shielding.

The needle assembly may further include biasing means for urging the shield from the proximal position to the distal position. The biasing means may comprise a coil spring disposed within the housing and extending between a portion of the hub and a portion of the shield. The spring may be in a compressed condition when the shield is in its proximal position. The spring then is operative to propel the shield to the distal position.

Actuating means are provided for releasing the shield from the proximal position and enabling the biasing means to propel the shield to the distal position. The actuating means may be actuated automatically and passively in response to an operational condition indicative of use of the needle assembly. For example, the needle assembly intended for use with an evacuated tube may have an actuating means that is triggered by the movement of the evacuated tube into communication with the proximal end of the needle cannula. Alternatively, the actuating means may comprise a latch that is accessible at an external location such as on the hub or housing.

The needle assembly of the present invention enables a medical practitioner to hold portions of the housing that surround the shield during venipuncture. Thus, the medical practitioner is able to grip a portion of the needle assembly relatively close to the distal end of the needle cannula. Gripping may be facilitated by structural elements disposed externally on the housing. Thus, for example, the housing may include at least one flat dimensioned and disposed for convenient gripping. Alternatively, the housing or hub may be provided with corrugations, dimples, recesses, concave surfaces, roughening or other structure that will facilitate manual gripping by a medical practitioner.

The safety shield preferably includes a slide back actuator that permits the safety shield to be moved from an intermediate position back to the proximal position. However, the slide back actuator does not permit the safety shield to be moved after the safety shield has been locked in the distal position. The slide back actuator is configured to be manipulated digitally by the medical practitioner. Thus, the slide back actuator may include a finger tab disposed at a location proximally of the distal end of the safety shield. The finger tab is configured to be engaged efficiently by an index finger or thumb of a medical practitioner to permit the safety shield to be moved proximally relative to the needle cannula. The slide back actuator enables a medical practitioner to move the safety shield back into a proximal position that permits visual assessment of the depth of insertion of a needle cannula. This proximal movement of the safety shield can be opposed by forces exerted by a spring that propels the safety shield distally and into a shielding position relative to the distal end of the needle cannula.

DESCRIPTION OF THE DRAWINGS

FIG. 5 is an exploded view of the cannula and hub sub-assembly as it fits within the housing and holder sub-assembly.

FIG. 6 is a partially exploded view of the cannula and hub sub-assembly aligned for assembly with the housing.

FIG. 7 is a magnified view of the portion of FIG. 6 showing the proximal end of the housing with snap retainers.

FIG. 8 is an exploded perspective view of a needle assembly with detached holder of the present invention.

FIG. 9 is an exploded perspective view of the needle assembly in FIG. 8 with non-patient shield detached.

FIG. 10 is an exploded perspective view of the needle assembly in FIG. 8 with the packaging and non-patient shields removed from the housing.

FIG. 11A is a front view of the housing of the present invention.

FIG. 11B is a sectional perspective view of the housing cut along the line depicted in FIG. 11A.

FIG. 11C is a sectional perspective view of the housing cut along the line depicted in FIG. 11A.

FIG. 12A is perspective view of the safety shield of the present invention.

FIG. 13 is an elevation view of the actuator of the present invention.

FIG. 14 is a perspective view of the actuator of the present invention.

FIG. 17 is an elevation view of the needle assembly during use before shielding.

FIG. 18 is an elevation view of the needle assembly after shielding.

FIG. 19A is a sectional view of the present invention shown before actuator safety shield release.

FIG. 19B is a sectional view of the present invention shown during actuator safety shield release.

FIG. 19C is a sectional view of the present invention shown after actuator safety shield release but prior to complete shielding.

FIG. 19D is a sectional view of the present invention shown after actuator safety shield release and after complete shielding.

FIG. 20A is a perspective sectional view of the present invention shown before actuator safety shield release.

FIG. 20B is a perspective sectional view of the present invention shown during actuator safety shield release.

FIG. 20C is a perspective sectional view of the present invention shown after actuator safety shield release but prior to complete shielding.

FIG. 20D is a perspective sectional view of the present invention shown after actuator safety shield release and after complete shielding.

DETAILED DESCRIPTION

Figure 1:
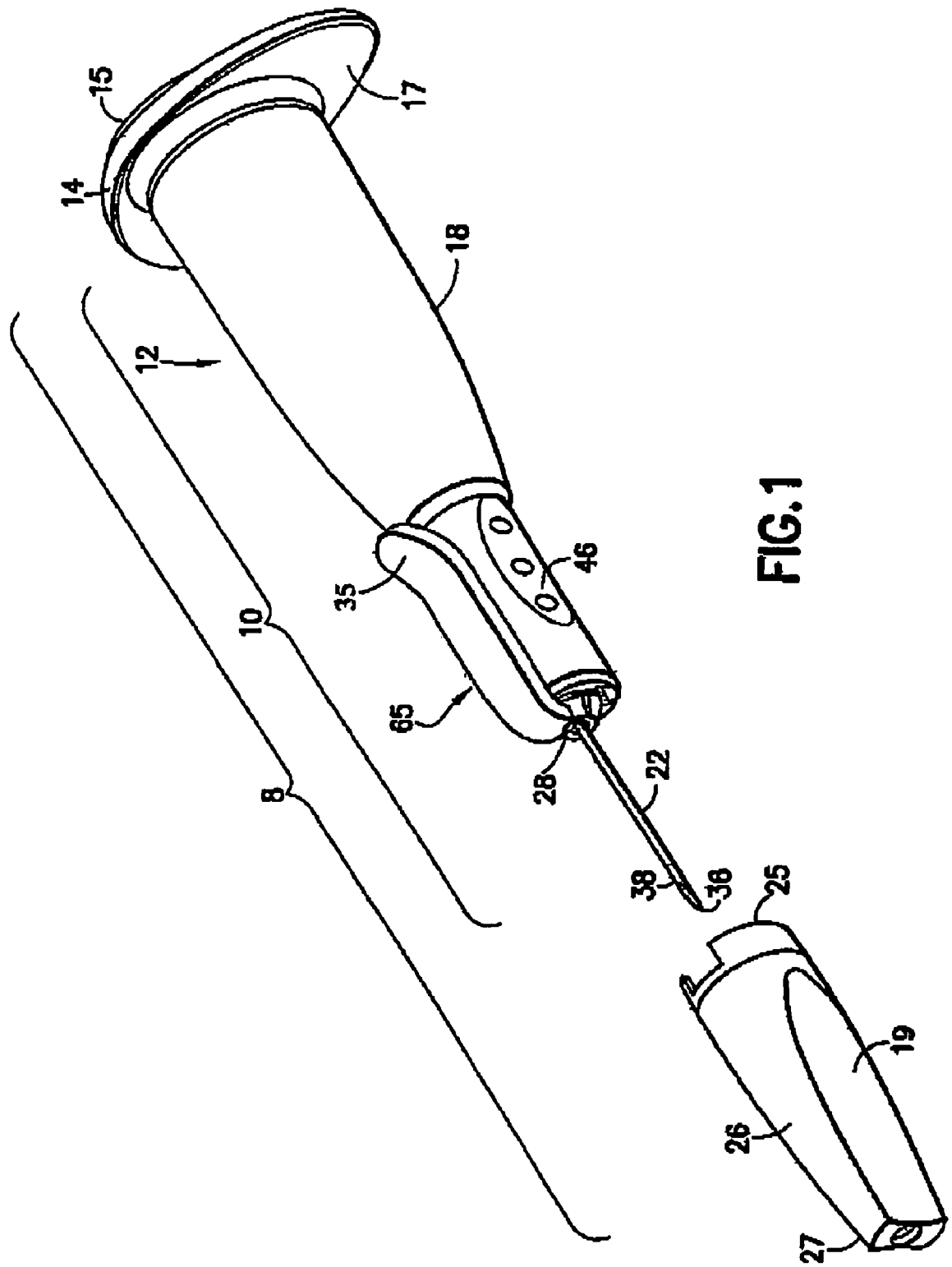
FIG. 1 is a perspective view of the needle assembly of the present invention.
Figure 2:
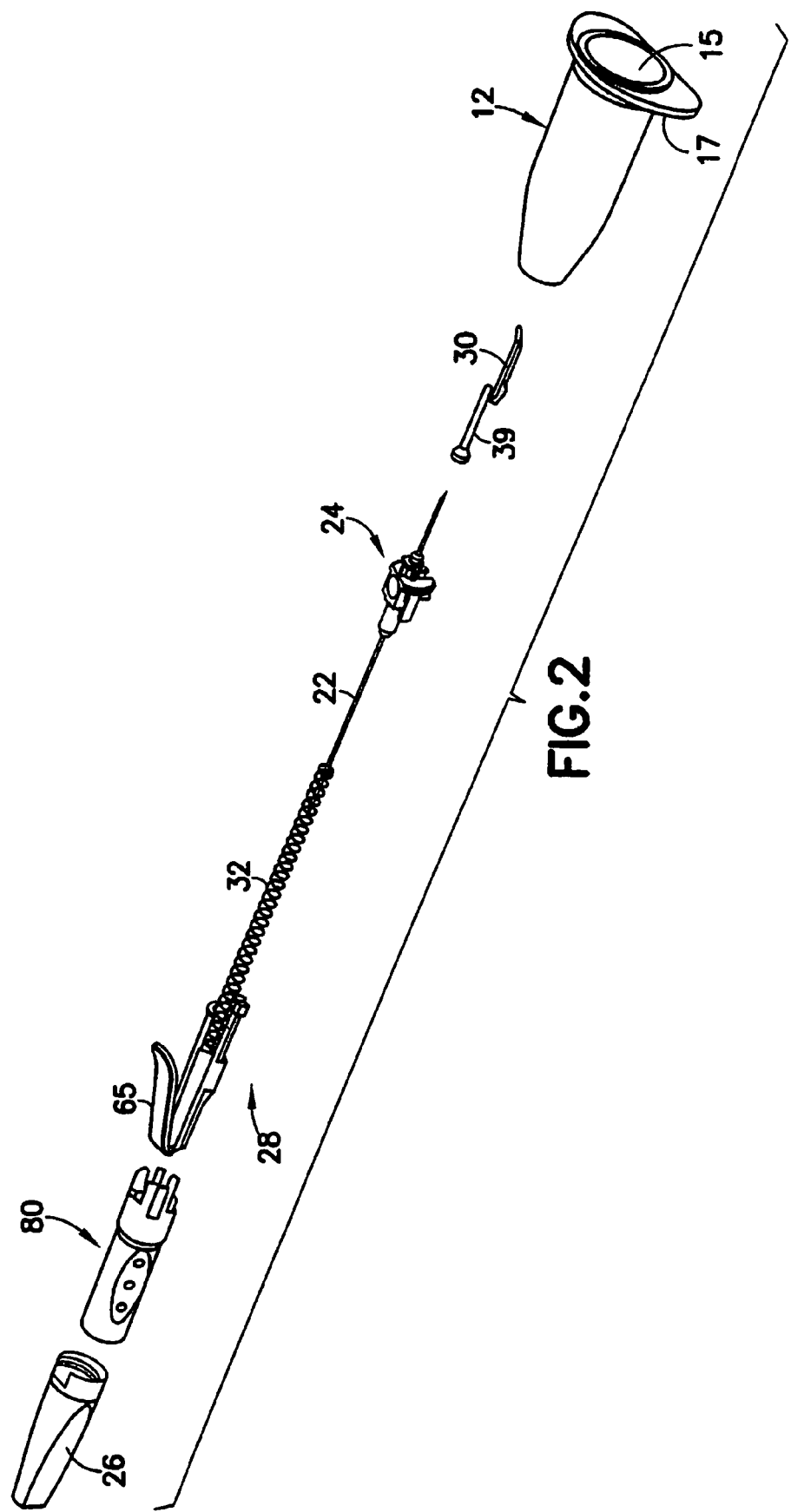
FIG. 2 is an exploded view of the device shown in FIG. 1.
Figure 3:
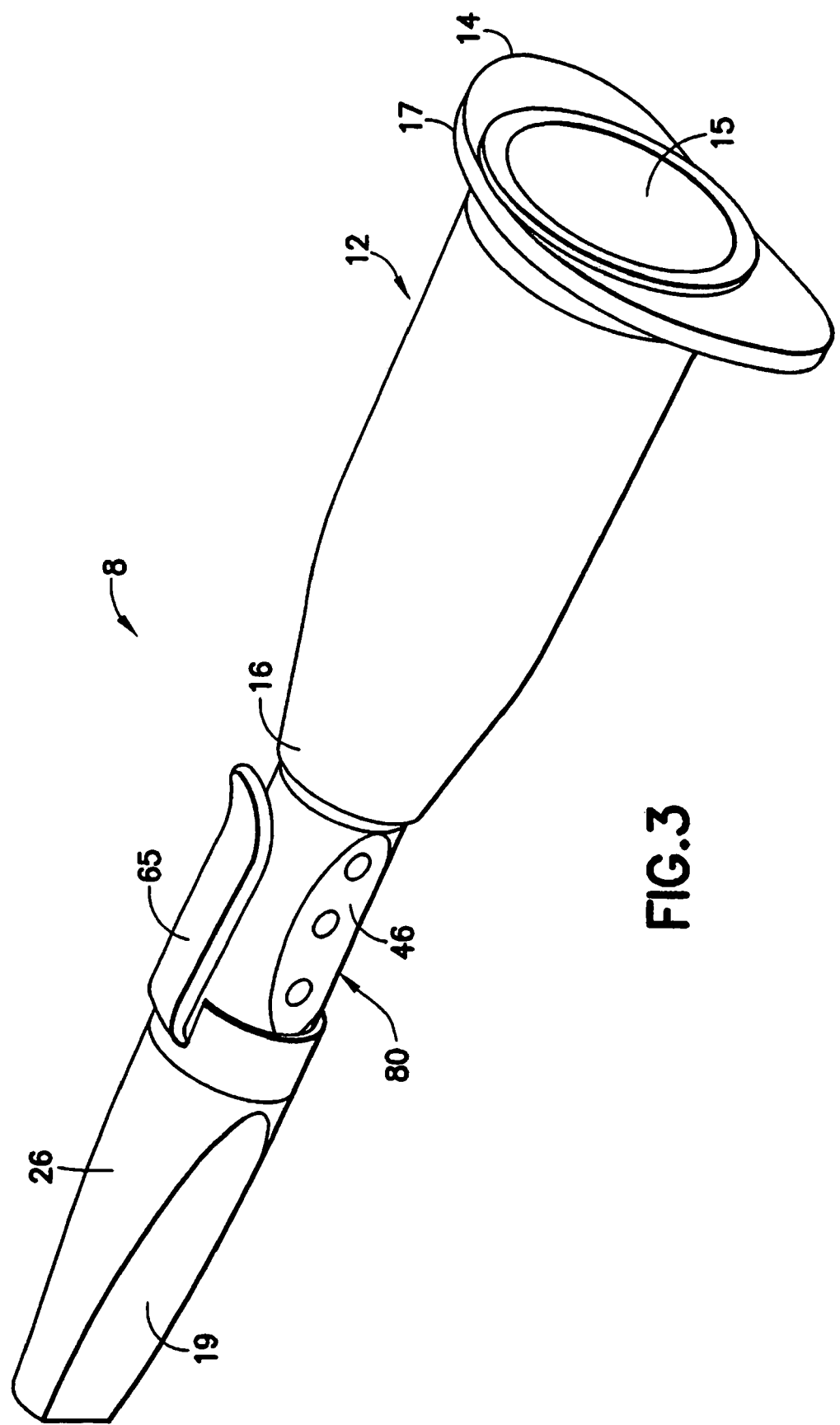
FIG. 3 is a perspective view with the packaging shield covering the needle cannula before use.
Figure 4:
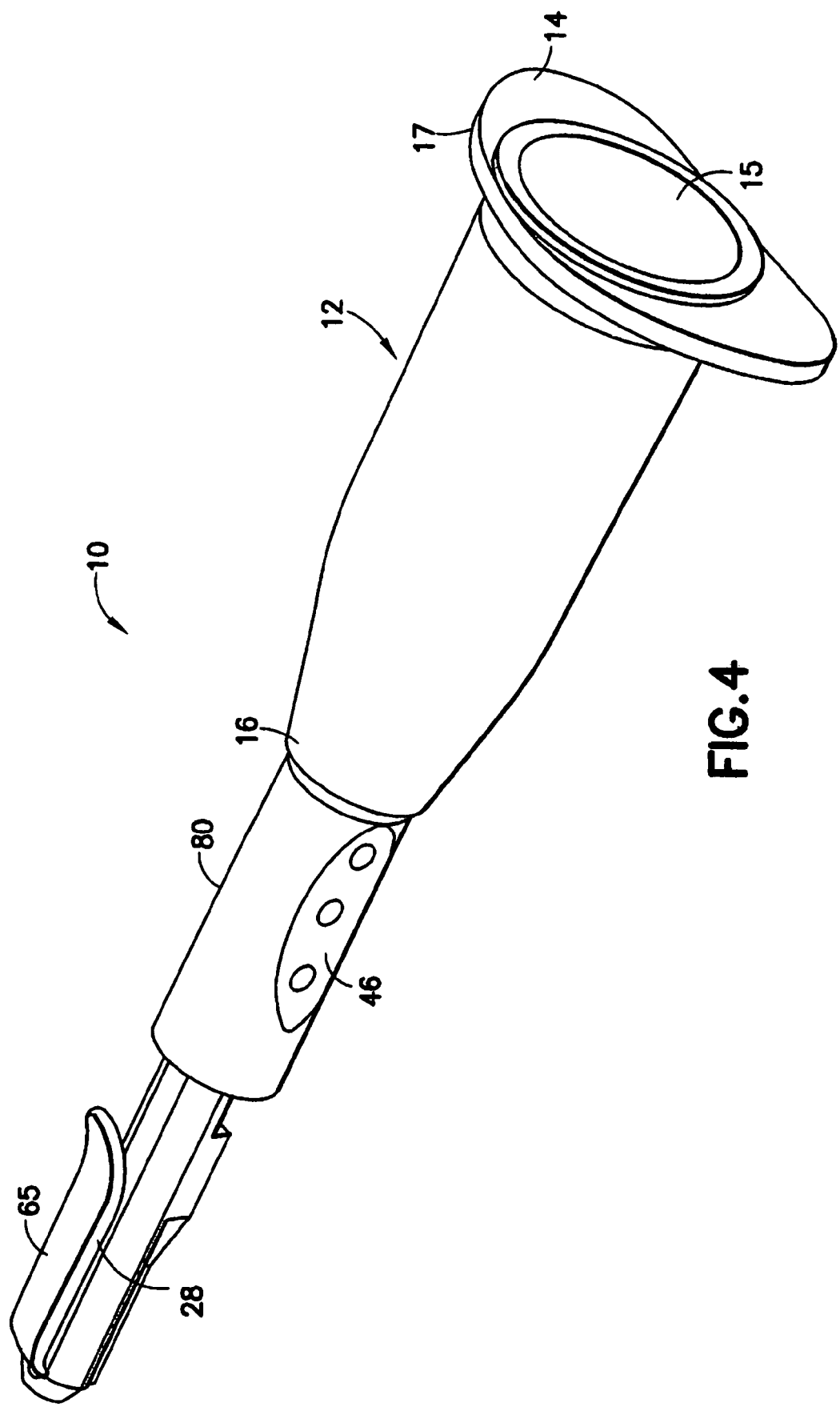
FIG. 4 is a perspective of FIG. 1 with the needle shield covering the needle cannula after use.

The needle assembly 10 of the present invention is shown in FIGS. 1–7 and 11–20. It will be noted that the term "distal" as used herein refers to the end of the needle assembly that punctures the patient's skin while "proximal" means the end of the needle assembly that punctures an evacuated container. Needle assembly 10 is mounted to a needle holder 12, as shown in FIGS. 1, 3, and 4. Needle holder 12 has a proximal end 14, a distal end 16 and a tubular sidewall 18 extending between ends 14 and 16. Proximal end 14 of needle holder 12 is widely open and is adapted to receive a blood collection tube 20 as shown in FIGS. 17, 19A–19D, and 20A–20D. However, proximal end 14 of holder 12 may have a removable seal or cap 15 for sterility. Proximal end 14 of holder 12 also has a radially aligned finger flange 17 to facilitate manipulation of holder 12. Flange 17 is non-circular to prevent holder 12 from rolling. Flange 17 preferably has a linear edge to provide a clear indication of the top and bottom sides. Distal end 16 of needle holder 12 includes structure to which needle assembly 10 is mounted. In particular, distal end 16 of needle holder 12 may be formed with non-threaded mounting means, such that needle holder 12 is substantially fixed to needle assembly 10 after assembly. The non-threaded mounting means comprises a combination of external rings 81 and keyways to secure needle assembly 10 axially and circumferentially. It is preferred that needle assembly 10 is mounted to needle holder 12 by the manufacturer so that the device is ready for fast and convenient use. Most importantly, pre-assembled needle assemblies 10 and needle holders 12 ensure that the proximal point of the needle is enclosed within holder 12 before, during, and after blood collection. Alternately, however, the distal end of the needle holder may be formed with an internal array of threads that are engagable by external threads on the needle assembly.

Needle assembly 10 ideally is packaged in a blister package having a thermoformed blister and top web. The top web is comprised of a material that may be permeable to gas such as ethylene oxide gas. Optionally, the proximal end 14 of holder 12 can be covered with a paper-like membrane that is thermally or adhesively sealed onto the proximal end 14 of the holder. Examples of materials used for a paper-like membrane are Tyvek® manufactured by DuPont and examples of materials to be used for a thermoformed blister package include glycol modified polyethylene terephthalate (PETG), polyethylene terephthalate (PET), high-density polyethylene, polypropylene, polycarbonate, nylon, and K-resin. In the configuration with a paper-like membrane covering the open proximal end 14 of holder 12, a thermoformed blister and top web would not be required, and the entire assembly can be sterilized by ethylene oxide gas or cobalt 60 irradiation.

Needle assembly 10 includes a needle cannula 22, a needle hub 24, a packaging shield 26, a safety shield 28, a sleeve 39, a housing 80, a release actuator 30, and a spring 32. In other embodiments, a portion of the needle assembly (e.g., the housing) can be integral or unitary with the needle holder to reduce assembly steps by the manufacturer and the user.

Needle cannula 22 includes a pointed proximal end 34, as shown in FIGS. 1, 5 and 6, a sharply beveled distal end 36 and a lumen 38 extending therebetween. Proximal end 34 of needle cannula 22 is covered by an elastomeric multiple sample sleeve 39 (shown in FIGS. 2, 9 and 10) that can be pierced by pointed proximal end 34 of needle cannula 22.

Figure 15:
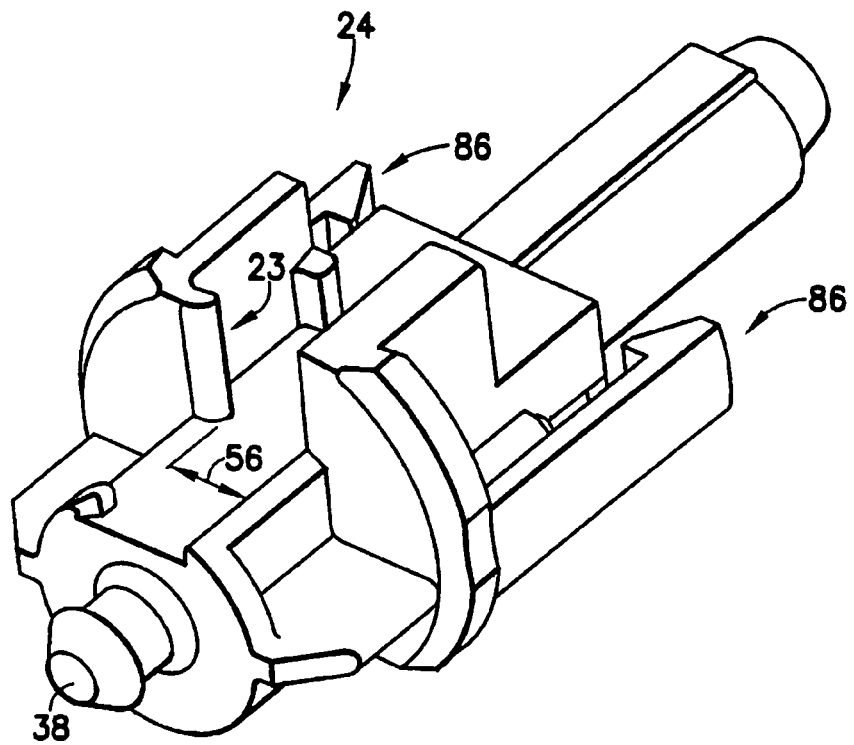
FIG. 15 is a perspective view of the hub of the present invention.
Figure 16:
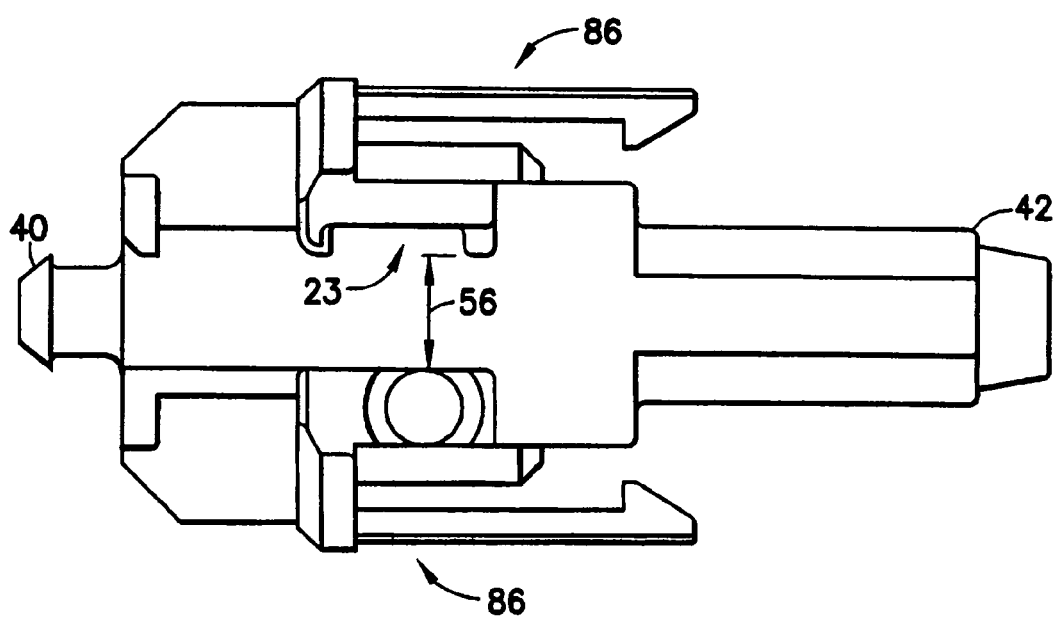
FIG. 16 is an elevation view of the hub of FIG. 15.
Figure 21:
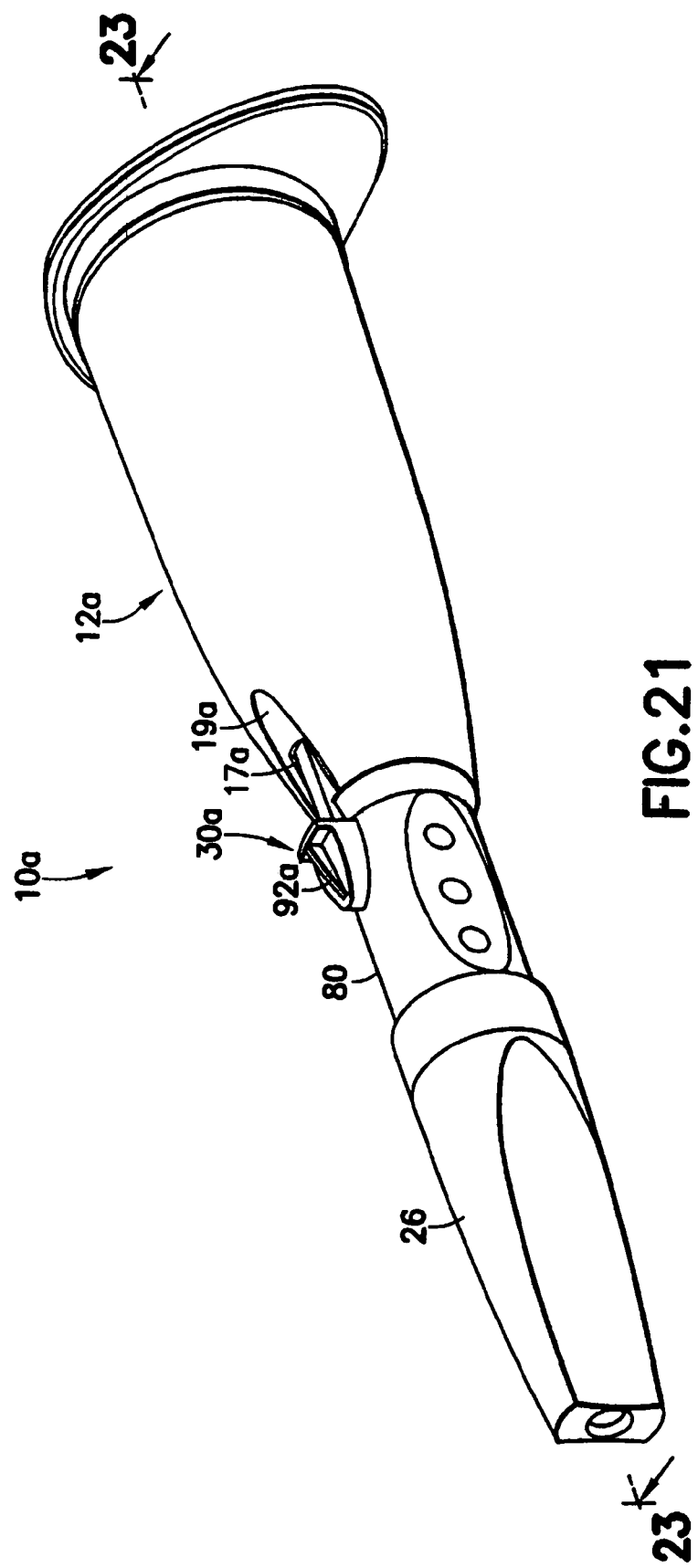
FIG. 21 is a perspective view of an alternate needle assembly of the present invention prior to use and with the packaging shield covering the needle cannula.
Figure 22:
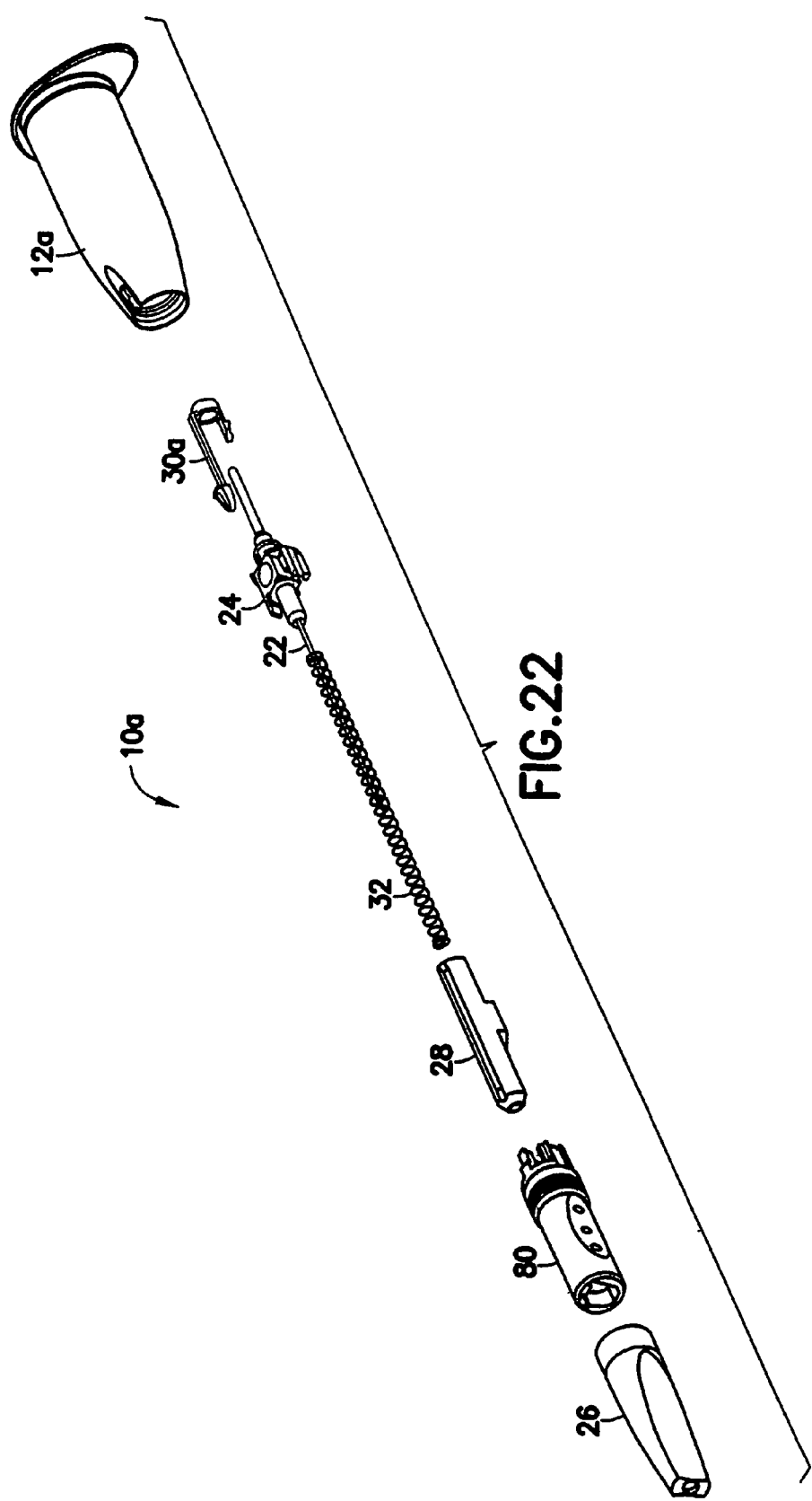
FIG. 22 is an exploded perspective view similar to FIG. 2, but showing the alternate embodiment of FIG. 21.
Figure 23:
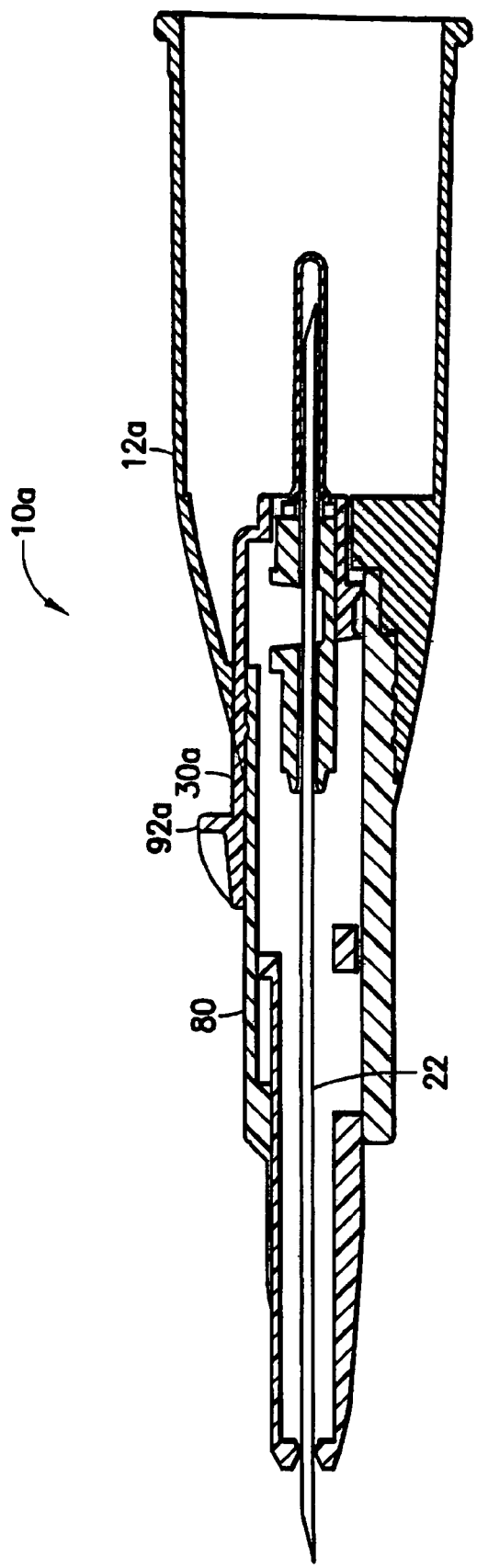
FIG. 23 is a cross-sectional view taken along line 23—23 in FIG. 21.

Needle hub 24 is illustrated in greater detail in FIGS. 15 and 16. Needle hub 24 includes a proximal end 40, a distal end 42, and a lumen 38 extending therebetween. Housing attachment means is provided externally of hub 24 to achieve fixed engagement between hub 24 and needle housing 80. The housing attachment means may include ultrasonic welding, heat staking, solvent bonding, mechanical latches with receiving latch detents, adhesive bonding, friction fit joints, irreversible threads, or any of the like. In the embodiment of FIGS. 5, 6, 7, 15 and 16 the housing attachment means are defined by mechanical latches 86 that extend distally from needle hub 24 for engagement in detents 88 on needle housing 80. Hub 24 is mounted securely to locations on needle cannula 22 between proximal and distal ends 34 and 36 thereof and in a specified rotational orientation relative to the bevel at distal end 36 of needle cannula 22. More particularly an adhesive well is formed on needle hub 24 and receives adhesive to bond needle cannula 22 to hub 24. Alternately, needle hub 24 and needle housing 80 may be combined as one molded component. However it is generally easier to manufacture needle hub 24 and housing 80 as two components.

Needle housing 80 is illustrated in greater detail in FIGS. 11A–11C. Needle housing 80 includes a proximal end 82, a distal end 84 and a tubular wall 44 extending between ends 82 and 84. As shown in FIGS. 11A–11C, tubular wall 44 is of generally circular or elliptical cross-section. Alternately, tubular wall 44 may have a non-circular cross-section or rectangular cross-section. The specific cross-sectional shape is not critical, and shapes other than those shown herein are contemplated. Housing 80 preferably is formed from a transparent or translucent material to permit user observation of safety shield 28. Thus, the medical practitioner can observe movement of safety shield 28, as explained below, to provide a visual indication that proper shielding is taking place. Additionally, proximal end 82 of housing 80 may have one of many optional means for attachment to a needle holder 12, such as a threaded connection, interference fit, adhesive bonding, solvent bonding, ultrasonic welding, heat staking, snap fit, or any other means. More specifically, the housing may have external threads and may be mounted to internal threads of the distal end of the needle holder. Alternately, housing 80 has non-threaded mounting means to engage holder 12 in an interlocking manner. External rings 81 are illustrated in FIGS. 5–7 and define one preferred non-threaded mounting means that provide sufficient frictional or interlocking forces to resist housing 80 from unintentionally releasing from holder 12 during puncturing of septum 21 by proximal end 34 of needle cannula 22. In the illustrated embodiment, hub 24 is mounted indirectly to the holder 12 through needle housing 80. Housing 80 preferably is non-rotatably mounted to holder 12 to ensure that the bevel at distal end of needle cannula 22 faces up relative to the bottom edge of flange 17 of holder 12. Distal end 84 of needle housing 80 is characterized by diametrically opposed V-shaped notches as shown in FIG. 11B. Notches 85 cooperate with corresponding structure on packaging shield 26.

Housing 80 has a length such that distal end 84 of housing 80 is spaced proximally from distal end 36 of needle cannula 22 sufficiently to enable convenient use of needle cannula 22. Portions of tubular wall 44 from distal end 84 toward proximal end 82 of housing 80 are spaced outwardly from needle cannula 22 for permitting telescoped movement of safety shield 28 between needle cannula 22 and housing 80, as explained further below. Additionally, as shown in FIGS. 1, 3, and 4, tubular sidewall 44 of housing 80 is provided with external surface configurations or grips 46 to facilitate digital manipulation. Surface configurations or grips 46 include elongate recesses or flats having small bumps thereon. However, other surface configurations may be employed, such as a plurality of ridges or grooves, or concave detents shaped to conform to a user's fingers. Grips 46 preferably are orthogonal to the bottom edge of finger flange 17 of holder 12.

Housing 80 has internal features to restrict movement of safety shield 28 relative to housing 80. Tubular wall 44 of housing 80 is formed with a first proximal facing stop surface 48. As shown in FIG. 11B, housing 80 further includes an axially extending latch channel 52 formed on an upper interior surface of tubular wall 44. Latch channel 52 extends from the first proximal facing stop surface 48 shown in FIG. 11C to a location substantially adjacent distal end 84 of housing 80 as shown in FIG. 11B. A distal detent 47 is located near the distal end of tubular wall 44 of housing 80, as shown, and is at the distal end of latch channel 52. Distal detent 47 has a distally facing stop surface 54. Distal detent 47 and distally facing stop surface 54 are dimensioned to receive a latch 68 on safety shield 28, as explained below. Tubular wall 44 further includes a stop channel 50 extending distally and ending with a second proximally facing stop surface 58 near distal end 82 of housing 80 as shown in FIG. 11C.

Distal end 36 of needle cannula 22 is used to pierce the patient's skin and must be kept very sharp. Thus a packaging shield 26, as shown in FIGS. 1–3 and 8–10, is used to enclose the distal end 36 of needle cannula 22. The packaging shield 26 preferably is formed with two opposing relatively flat walls 19 to facilitate easy handling by the phlebotomist who is likely to be wearing gloves that may even be wet with alcohol prep solution. In the embodiment shown, the open end of the packaging shield 26 fits partially over the distal end 84 of housing 80. The packaging shield 26 and housing 80 are dimensioned so that there is an interference fit that desirably provides a sterile barrier between the packaging shield 26 and housing 80 in those embodiments that do not employ blister packaging. In those embodiments, the interference fit between packaging shield 26 and housing 80 they make separation of packaging shield 26 difficult. Accordingly, for those embodiments, packaging shield 26 is provided with a pair of diametrically opposed ribs (not shown) on the interior surface. The ribs terminate at a V-shaped point or an arcuate end facing toward the open end of packaging shield 26. The ends of the ribs are disposed, dimensioned and configured to mate with the V-shaped notches 85 at distal end 84 of housing 80. The engagement of the ends of the rib with V-shaped notches 85 develops ramping forces in response to twisting of packaging shield 26. Thus, the rotational movement applied to packaging shield 26 generates a corresponding axial movement of packaging shield 26 relative to housing 80, and hence facilitates separation of packing shield 26. Additionally, a tamper-evidence indicator may be placed between the packaging shield 26 and the housing 80 to provide indication of prior usage.

Safety shield 28, as shown in FIGS. 12A–12D, includes a proximal end 60, a distal end 62 and a substantially tubular sidewall 64 extending between the ends. Tubular sidewall 64 of safety shield 28 preferably is imprinted with indicia at a location aligned with the bevel-up side of needle cannula 22. This is the portion of tubular sidewall 64 that will be the most visible to the medical practitioner. The existence of indicia on this portion of tubular sidewall provides a physical indication to the medical practitioner that shielding is taking place. The indicia should be in a form that will provide evidence of movement. For example, a plurality of intermittent markings or a marking that changes its dimensions along its length would be most beneficial. Safety shield 28 initially is retained releasably in a proximal position with at least a major portion of safety shield 28 disposed in the space between needle cannula 22 and tubular wall 44 of housing 80. In this proximal position, proximal end 60 of safety shield 28 is substantially adjacent first proximally facing stop surface 48 of housing 80. Additionally, as shown in FIG. 1, distal end 62 of safety shield 28 is flush with or projects only slightly from distal end 84 of housing 80 when safety shield 28 is in its proximal position. Safety shield 28 can be released from its proximal position and is movable to a distal position that is shown in FIGS. 4, 18, 19D and 20D. When moved into its distal position, safety shield 28 completely covers portions of needle cannula 22 between needle hub 24 and distal end 36 of needle cannula 22. Safety shield 28 further includes an elongate slide back actuator 65 that is cantilevered in a proximal direction from a location on tubular sidewall 64 substantially adjacent distal end 62 of safety shield 28. Most of elongated slide back actuator 65 extends substantially parallel to tubular sidewall 64 and is spaced therefrom by a distance at least equal to the thickness of the resin material from which housing 80 is formed. Thus, slide back actuator can be slid along the external surface of housing 80 when tubular sidewall 64 of safety shield 28 is telescoped into housing 80. The proximal end of slide back actuator 65 includes an actuating surface 35. Actuating surface 35 is substantially concave and faces in a distal and outward direction on safety shield 28.

Figure 12B:
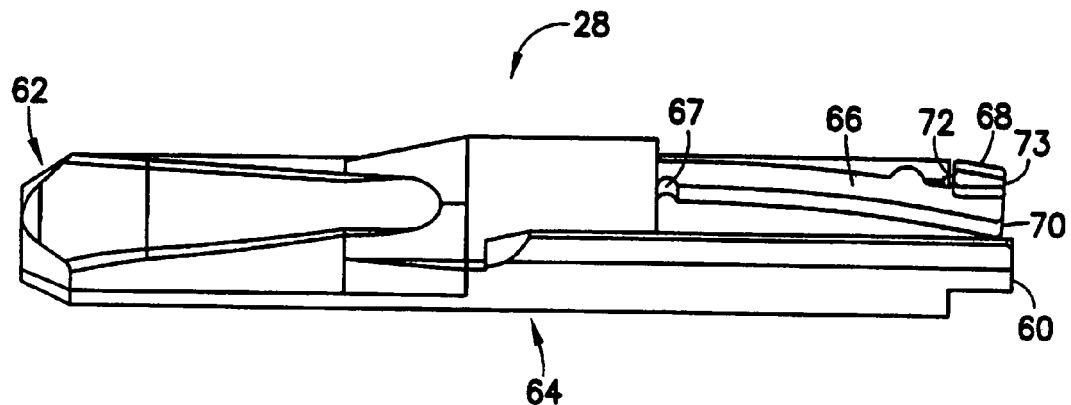
FIG. 12B is a perspective view of the needle shield of the present invention.
Figure 12C:
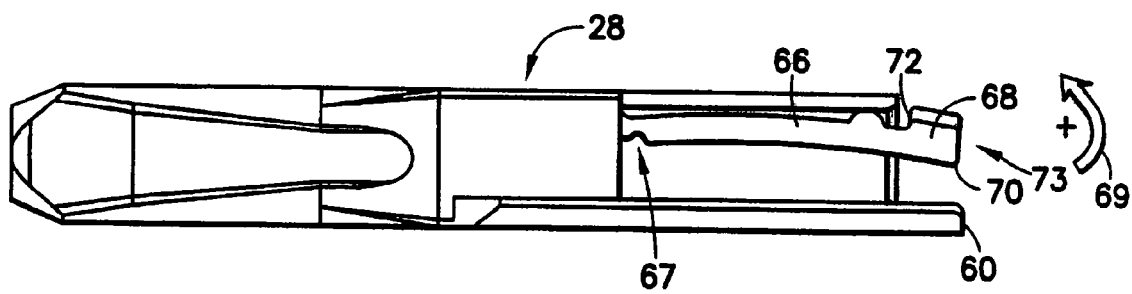
FIG. 12C is an elevation view of the needle shield of the present invention with the deflectable member in an unbiased position.
Figure 12D:
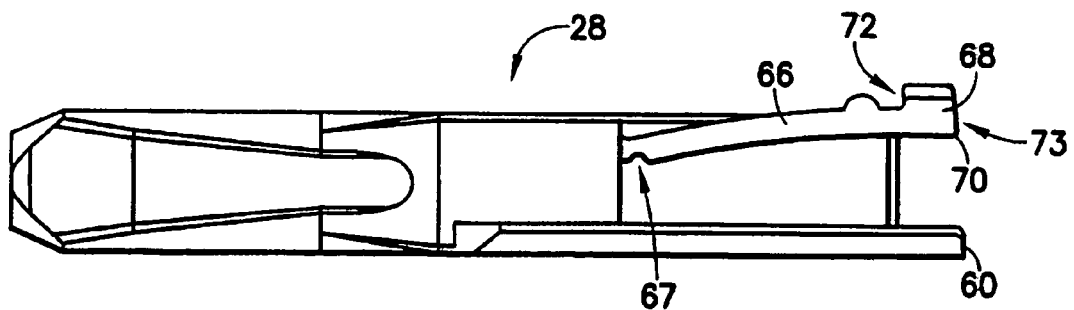
FIG. 12D is an elevation view of the needle shield of the present invention similar to FIG. 12C, but with the deflectable member in a deflected state.

As shown in FIGS. 12B–12D, safety shield 28 has a hinged deflectable member 66 that is cantilevered toward proximal end 60. Deflectable member 66 is deflectable outwardly or in a transverse direction. A latch 68 is formed on deflectable member 66 near proximal end 60 of safety shield 28 and enters latch channel 52 when deflectable member 66 is deflected outwardly. Hinged deflectable member 66 further includes a cam surface 70 at the extreme proximal end thereof. Cam surface 70 is aligned at an acute angle to a radial plane passing through needle assembly 10. Axially aligned distally directed forces on cam surface 70 will generate a transverse deflection of deflectable member 66 so that latch 68 enters into latch channel 52. Latch 68 further includes a distal facing locking face 72, and a proximally facing locking face 73. Both locking faces 72 and 73 are aligned substantially perpendicular to the axis of needle assembly 10. FIG. 12C shows deflectable member 66 in its non-deflected state and FIG. 12D shows deflectable member 66 in its deflected state. Distal movement of release actuator 30 moves deflectable member 66 from the position shown in FIG. 12C in direction 69 depicted in FIG. 12C to the position shown in FIG. 12D until latch 68 is no longer resisted by first proximally facing stop surface 48 of housing 80 and therefore is free to move distally with respect to the needle cannula 22 under spring energy supplied by spring 32.

Safety shield 28 further includes a stop 74 disposed substantially diametrically opposite latch 68. Stop 74 is in a plane passing through the axis of needle assembly 10 and includes a locking surface 76 facing in the distal direction as shown in FIG. 12A. Stop 74 prevents spring 32 from pushing safety shield 28 past housing 80.

Hub 24 is connected to the proximal end 82 of housing 80. Hub 24 further includes an actuator channel 56 extending substantially parallel to housing 80 as shown in FIGS. 15 and 16. Release actuator 30, as shown in FIGS. 13 and 14, is disposed slidably in actuator channel 56 of hub 24. Release actuator 30 includes a proximal end 78 substantially adjacent to needle cannula 22 that will lie within needle holder 12. Release actuator 30 also includes a distal end 79 that will lie substantially adjacent cam surface 70 of latch 68. Distal end 79 of release actuator 30 is angularly aligned to mate with cam surface 70 of latch 68, such that distal movement of release actuator 30 will generate transverse deflection of deflectable member 66.

As shown in FIGS. 13 and 14, release actuator 30 has an integrated anti-reset feature or latch 29 that interfaces with hub 24 upon activation of the device. Once a tube 20 is inserted and interfaces with the proximal end 78 of release actuator 30, latch 29 will interface with the hub channel 56 thus deforming latch 29 temporarily inward thereby permitting latch 29 to advance into latch recess 23. Once latch 29 is within latch recess 23, latch 29 will return resiliently towards an undeflected position so that release actuator 30 is prevented from moving back to a proximal position that would allow safety shield 28 to be completely reset to its original position.

A spring 32 surrounds portions of needle cannula 22 that are surrounded by safety shield 28. Thus spring 32 is compressed to retain stored energy when safety shield 28 is in the proximal position within tubular wall 44 of housing 80. Spring 32 then will propel safety shield 28 distally after activation. The proximal end 31 of spring 32 remains in fixed relation to the holder 12, hub 24, and housing 80 while the distal end 33 of spring 32 moves relative to the holder 12, hub 24, and housing 80.

The force applied by spring 32 to safety shield 28 is essential to proper operation of needle assembly 10. In particular, spring 32 must exert sufficient force to ensure that safety shield 28 will be propelled sufficiently toward distal end 36 of needle cannula 22 to complete its essential shielding function. However spring 32 should not exert enough force to push needle cannula 22 out of the patient. Additionally, forces exerted by safety shields 28 on the skin of the patient should not be so large as to cause a patient to react and move suddenly away from the shield. A spring force of 0.02–0.20 pounds, and preferably about 0.09 pounds has been found to meet the objectives of ensuring complete shielding without excessive force against the skin of the patient. Additionally, a fine lubricating spray may be applied to the sliding parts of safety shield 22, hub 24 and/or housing 80 to ensure complete and efficient movement of safety shield 28 with a low spring force.

Needle assembly 10 is used by attaching proximal end of hub 24 and housing 80 into needle holder 12 such that proximal end 34 of needle cannula 22 and proximal end 78 of release actuator 30 lie within needle holder 12. In this condition, safety shield 28 is retained in the proximal position with a major portion of tubular sidewall 64 disposed in the space between needle cannula 22 and tubular wall 44 of housing 80. However, slide back actuator 65 extends proximally from distal end 62 of safety shield 28 and along the exterior of housing 80 to a position between distal end 84 of housing 80 and needle holder 12. In this position, pointed distal end 36 of needle cannula 22 projects distally beyond safety shield 28. However, pointed distal end 36 of needle cannula 22 is retained safely within packaging shield 26. Packaging shield 26 then is removed from housing 80 to expose pointed distal end 36 of needle cannula 22. The medical practitioner then manually engages housing 80 at grips 46 and guides distal end 36 of needle cannula 22 into a targeted vein of a patient. Activation of shield 28 is achieved automatically and passively by insertion of blood collection tube 20 into proximal end 14 of needle holder 12. Sufficient insertion of blood collection tube 12 will cause proximal end 34 of needle cannula 22 to pierce through the elastomeric septum 21 that extends across the open end of blood collection tube 20, as shown in FIGS 19A–19D. Distal movement of blood collection tube 20 into needle holder 12 also will cause blood collection tube 20 to engage proximal end 78 of release actuator 30, thereby causing release actuator 30 to slide distally through actuator channel 56 of hub 24. This distal movement of release actuator 30 will cause distal end 79 of release actuator 30 to engage cam surface 70 of hinged deflectable member 66 of safety shield 28 with sufficient force to pivot deflectable member 66 transversely about hinge 67 sufficiently to disengage locking face 72 of latch 68 from first proximally facing stop surface 48 of housing 80. Disengagement of latch 68 from first proximally facing stop surface 48 into latch channel 52 causes safety shield 28 to be propelled distally under the action of spring 32. Distal movement of safety shield 28 will terminate when distal end 62 of safety shield 28 moves into contact with the skin of the patient at locations substantially adjacent the injection site.

Blood will flow into blood collection tube 20 when proximal end 34 of needle cannula 22 pierces septum 21 of blood collection tube 20. After a sufficient volume of blood has been collected, blood collection tube 20 will be withdrawn from needle holder 12. This removal of blood collection tube 20 will cause multiple sleeve 39 to return to its initial configuration substantially surrounding proximal end 34 of needle cannula 22. As a result, multiple sample sleeve 39 effectively functions as a valve that stops the flow of blood from proximal end 34 of needle cannula 20. A new blood collection tube 20 then is inserted into proximal end 14 of needle holder 12. Sufficient insertion of blood collection tube 20 will deform multiple sample sleeve 39 again and will cause proximal end 34 of needle cannula 22 to pierce both multiple sample sleeve 39 and septum 21 of the new blood collection tube 20. In this manner, an additional sample of blood is collected in the new blood collection tube 20. This process is completed for collecting the required number of samples of blood.

The withdrawal of blood collection tube 20 from needle holder 12 and the insertion of a new blood collection tube 20 into needle holder 12 creates forces on needle assembly 10 that could move needle cannula 22 and change the depth and angle of insertion. For this reason, medical practitioners prefer to be able to visually gauge the depth and angle of insertion of needle cannula 22 periodically during the course of a blood collection procedure. This monitoring of the depth and angle of insertion of needle cannula 22 can be carried out by monitoring the length of needle cannula 22 exposed proximally of the insertion site. However, safety shield 28 is at an intermediate position during a blood collection procedure and obscures virtually all of needle cannula 22 between the patient's skin and housing 80. A medical practitioner can digitally engage activating surface 35 of slide back actuator 65 to move safety shield 28 proximally against the forces exerted by spring 32 and into the extreme proximal position. As a result, the medical practitioner performing the blood collection procedure readily can monitor the depth and alignment of insertion by observing the distance between the skin of the patient at the injection site and the position where needle cannula 22 emerges from distal end 62 of safety shield 28. The medical practitioner can release the digital grip on actuating surface 35 after the last of the blood collection tubes 20 has been inserted into needle holder 12. As a result, spring 32 will propel safety shield 20 into a position where distal end 62 of safety shield 28 contacts the skin of the patient substantially adjacent the injection site. Needle holder 12 and/or housing 80 can be pulled proximally after the last of the blood collection tubes 20 has been filled. As a result, spring 32 will propel safety shield 28 toward its extreme distal position. Latch 68 will be guided in latch channel 52 as safety shield 28 is moved toward distal end 84 of housing 80. Sufficient distal movement of safety shield 28 will cause latch 68 to engage in distal detent 47 of housing 80. While in distal detent 47, latch 68 interferes with distal facing stop surface 54 and prevents safety shield 28 from being unshielded. Additionally, stop 74 on safety shield 28 rides along stop channel 50 until stop 74 engages second proximally facing stop surface 58 thereby preventing safety shield 28 movement in the distal direction after needle point 36 has been shielded. As a result of stop 74 and latch 68, safety shield 28 is prevented from moving either distally or proximally from this locked position as shown in FIGS. 18, 19D, and 20D.

Figure 24:
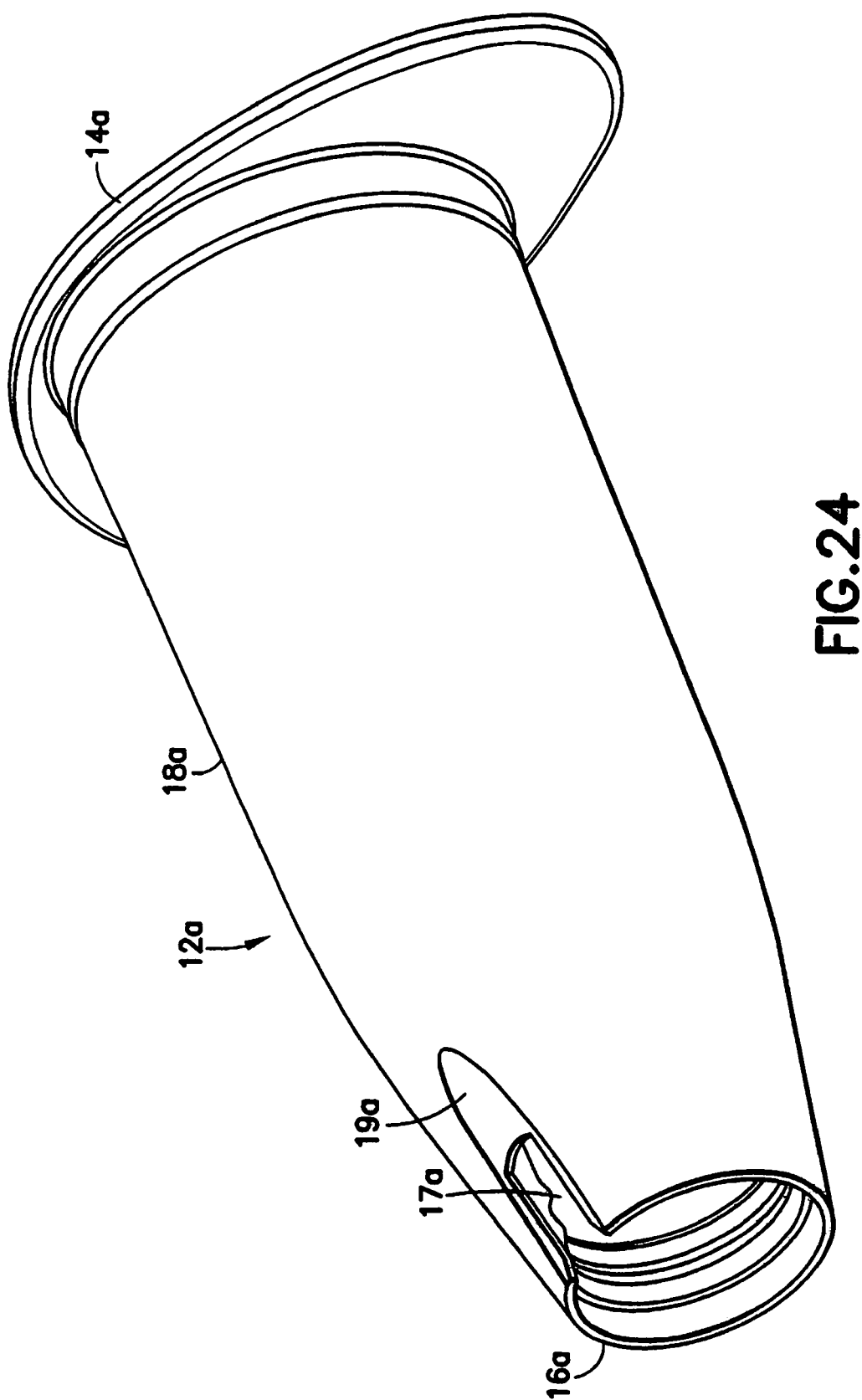
FIG. 24 is a perspective view of the holder for use with the embodiment of FIGS. 21–23.
Figure 25:
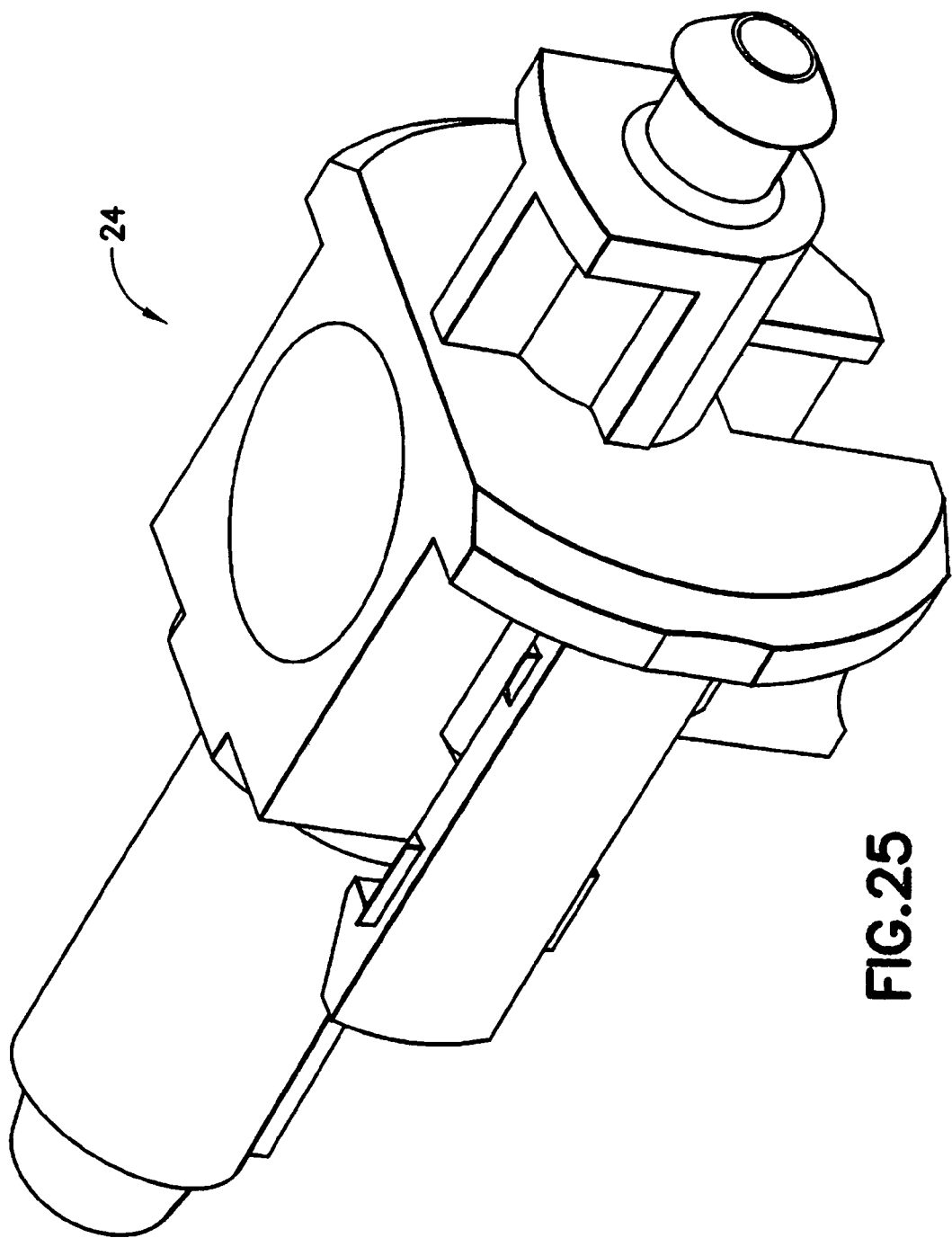
FIG. 25 is a perspective view of the hub for use with the embodiment of FIGS. 21–24.

The above-described needle assembly is completely passive in that shielding is achieved without any required user activation other than the normal insertion of a fluid collection tube into the open proximal end 14 of holder 12. There may be instances, however, where a user may want direct control over the initiation of shielding or where a user may want dual control where shielding can be actuated by insertion of a fluid collection tube and/or by direct digital activation by the user. These options can be achieved without a complete redesign of the above-described needle assembly. In particular, an alternate needle assembly is identified generally by the numeral 10a in FIGS. 21–27. Assembly 10a include a needle cannula 22, a hub 24, a packing shield 26 and a housing 80, all of which are substantially identical to corresponding parts of the first embodiment described and illustrated above. However, assembly 10a includes a holder 12a that is slightly different from holder 12 described and illustrated above. In particular, as shown most clearly in FIG. 24, holder 12a includes a tubular sidewall 18a that has a proximal end 14a, a distal end 16a. A notch 17a extends into tubular sidewall 18a at distal end 16a. Additionally, notch 17a is disposed on a portion of sidewall 18a that will align with the bevel-up side of needle cannula 22. Notch 17a is partly surrounded by an elongate flat or recess 19a in tubular sidewall 18a to minimize the projection of an actuator, as explained herein and to provide a visible indication of a region to be accessed by a user for carrying out a manual actuation of the shielding.

Figure 26:
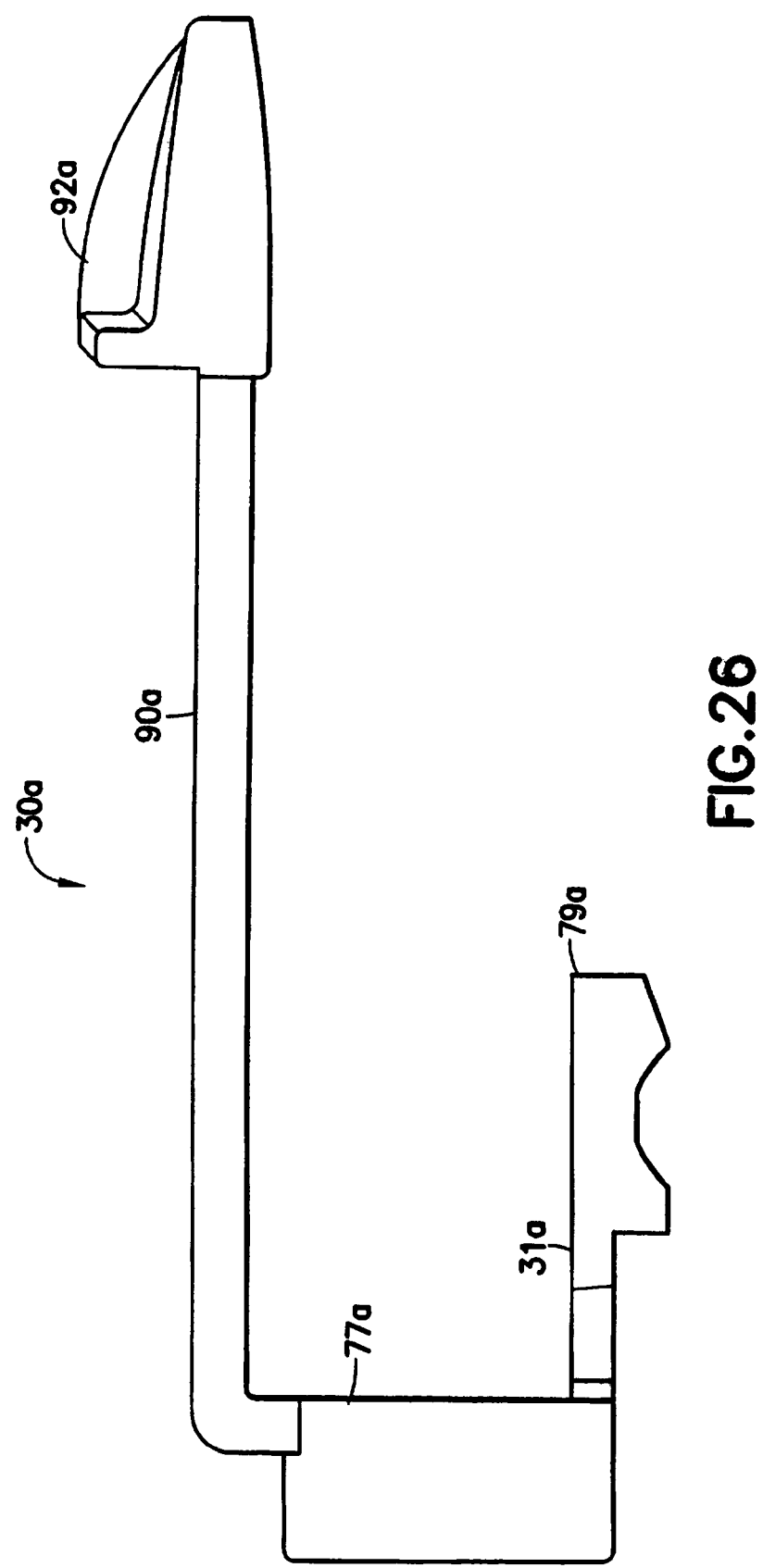
FIG. 26 is a side elevational view of the actuator of the embodiment of FIGS. 21–25.
Figure 27:
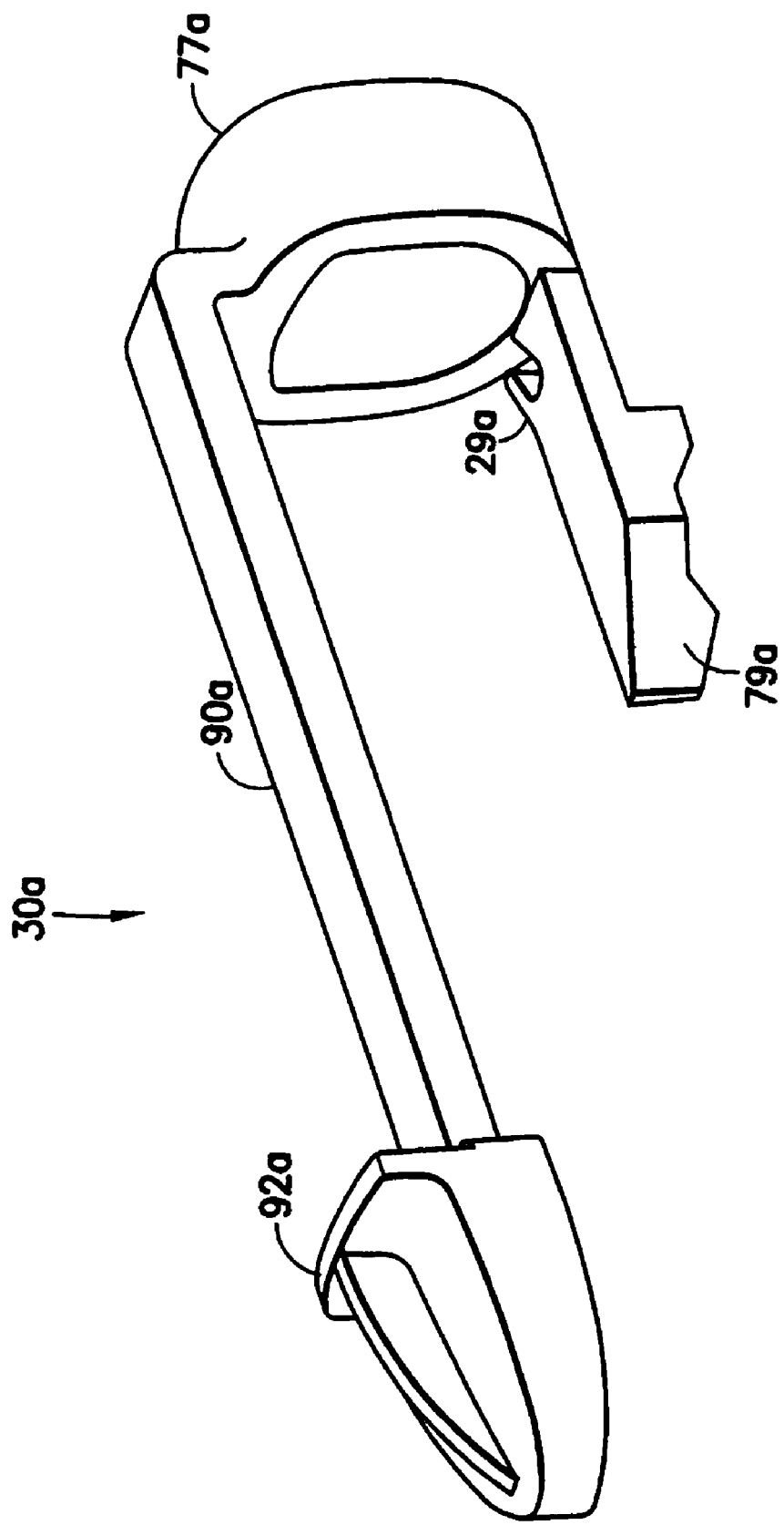
FIG. 27 is a perspective view of the actuator of FIG. 26.

Needle assembly 10a further includes an actuator 30a as shown in FIGS. 26 and 27, that differs from actuator 30 described above and illustrated in FIGS. 13 and 14. In particular, actuator 30a includes an actuating beam 31a with a distal end 79a that is structurally and functionally virtually identical to distal end 79 of actuator 30. Additionally, actuating beam 31a includes an anti-reset latch 29a that is structurally and functionally substantially identical to latch 29 of actuator 30. Actuator 30a further includes a mounting collar 77a that is disposed and configured to mount slidably over proximal portions of hub 24. Additionally, mounting collar 77a is dimensioned for slidable disposition within holder 12a. Actuator 30a further includes an arm 90a that projects distally from collar 77a. Arm 90a is dimensioned for slidable insertion in notch 17a of holder 12a, and terminates at an actuating button 92a.

Needle assembly 10a is assembled substantially as needle assembly 10, described and illustrated above. However, collar 77a of release actuator 30a is slidably disposed over and around proximal portions of hub 24. The subassembly of needle cannula 22, hub 24, packing shield 26, housing 80 and release actuator 30a can be mounted in holder 12a substantially as described above. However, arm 90a will project slidably through notch 17a such that actuating button 92a is slidably disposed on the outer circumferential surface of housing 80.

Needle assembly 10a is used substantially in the conventional manner as explained above. However, safety shield 28 is actuated by digital pressure exerted by a thumb or forefinger of the user on actuator button 92a. In particular, the user urges actuator button distally along outer surface of housing 80 a sufficient distance for distal end 79a of release actuator 30a to actuate safety shield 28 as explained above.

Figure 28:
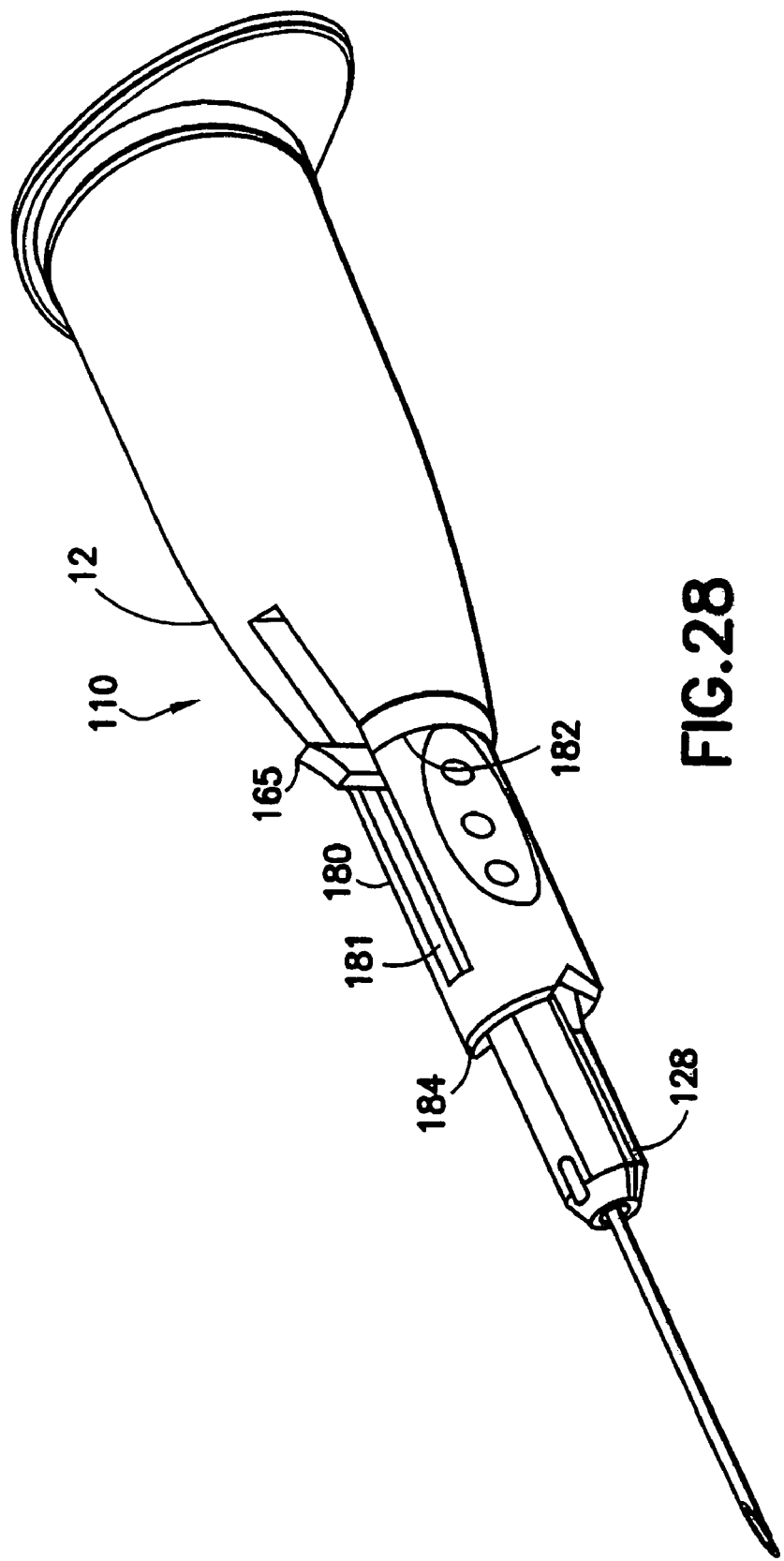
FIG. 28 is a perspective view of a needle assembly with an integrated slide back actuator.

FIG. 28 shows a variation of the embodiment depicted in FIG. 1 and described above. More particularly, FIG. 28 shows a needle assembly 110 with a needle holder 12 substantially identical to the needle holder 12 described and illustrated above. Needle assembly 110 also includes a housing 180 similar to the housing 80 described and illustrated above. However, housing 180 includes an elongate slot 181 that extends parallel to the axis of needle cannula 22 from a position near proximal end 182 of housing 180 to a position at or near distal end 184 of housing 180. Needle assembly 110 further includes a safety shield 128 with a slide back actuator 165 that projects through slot 181 in housing 180. Slide back actuator 165 can be actuated digitally to slide safety shield 128 in a proximal direction after venous access has been achieved to facilitate monitoring the depth and alignment of needle cannula 22.

As an alternate to the embodiments described above, the needle assembly can be made in a detachable holder or hard pack assembly 100 configuration using all the components of the needle assembly described above with the addition of a non-patient needle shield 90 for enclosing proximal end 34 of needle cannula 22 shown in FIGS. 8–10. Non-patient needle shield 90 is reversibly detachable to one or both of needle housing 80 and hub 24. The user removes non-patient needle shield 90 from hardpack assembly 100 and attaches holder 12 to the proximal end of housing 80 prior to use. Once holder 12 is attached to housing 80, the user can remove packaging shield 26 and use the needle device in a similar manner to the needle assembly embodiment described herein.

It will be apparent that other variations can be made to the present invention without departing from the scope of the invention as defined by the appended claims. In alternate embodiments, the actuator can deflect a latch radial inwardly or in some other direction to effect disengagement from the housing. In addition, the actuator and the latch may be configured to generate rotation of the shield relative to the housing for disengaging a latch on the shield from a detent on the housing. Still further, other configurations for the exterior of the housing may be provided for convenient and secure digital manipulation, such as the exterior of the shield may include an array of ribs, grooves or dimples instead of or in addition to the flats shown in the illustrated embodiments.

What is claimed is:

1. A medical device comprising:
   a piercing element having a piercing end;
   a safety shield releasably held in a proximal position on said medical device where said piercing end of said piercing element is exposed and being movable to a distal position where said piercing end of said piercing element is shielded;
   a release actuator movably disposed in said medical device and configured for passively releasing said safety shield from said proximal position in response to use of said medical device;
   a lock for locking said safety shield in said distal position;
   a slide back actuator for moving said safety shield from an intermediate position between said proximal and distal positions toward said proximal position;
   a spring for propelling said safety shield from said proximal position toward said distal position; and
   a holder configured for slidably receiving a fluid collection tube, said piercing element having a proximal end projecting into said holder for communicating with said fluid collection tube.

2. The medical device of claim 1, wherein said safety shield is telescoped over said piercing element for substantially linear movement from said proximal position to said distal position.

3. The safety device of claim 2, wherein said piercing element is a needle cannula.

4. The medical device of claim 1, wherein said release actuator extends into said holder and is configured for actuation by insertion of said fluid collection tube into said holder.

5. The medical device of claim 1, wherein the slide back actuator includes a distally and outwardly facing actuating surface.

6. The medical device of claim 1, wherein the slide back actuator is cantilevered proximally from a distal end of said safety shield.

7. The medical device of claim 1, wherein said safety shield is telescoped within a housing, said housing including an elongate slot formed therein and said slide back actuator projecting through said slot of said housing and being slidably movable said slot.

8. A blood collection device comprising:
   a hub;
   at least one needle cannula mounted to said hub and having a proximal end projecting proximally from said hub and a distal end projecting distally from said hub;
   a holder mounted to said hub and surrounding at least said proximal end of said cannula;
   a safety shield telescoped over said needle cannula for movement from a proximal position where said distal end of said needle cannula is exposed to a distal position where said distal end of said needle cannula is shielded;
   a spring for propelling said safety shield to said distal position;
   at least one lock for releasably holding said safety shield in said proximal position and for substantially permanently locking said safety shield in said distal position;
   a release actuator for releasing said safety shield from said proximal position passively in response to use of said blood collection needle assembly; and
   a slide back actuator extending from said safety shield for moving said safety shield proximally from an intermediate position between said distal and proximal positions, wherein said movement is capable of enhancing observation of said needle cannula during use.

9. The blood collection device of claim 8, further comprising a housing projecting distally from said holder and surrounding at least portions of said needle cannula, said safety shield being telescoped within said housing.

10. The blood collection device of claim 9, wherein said slide back actuator is cantilevered proximally from a distal end of said safety shield for movement substantially adjacent an external surface of said housing.

11. The blood collection device of claim 9, wherein said housing includes a longitudinal slot extending therethrough, said slide back actuator projecting from said safety shield and through said slot in said housing.

12. The blood collection device of claim 11, wherein said safety shield has opposite proximal and distal ends, said slide back actuator extending from said proximal end of said safety shield.

13. The blood collection device of claim 9, wherein said release actuator extends into said holder and is configured for engagement by insertion of a blood collection tube sufficiently into said holder for communicating with said proximal end of said needle cannula.

* * * * *